US012029681B2

(12) United States Patent
Bruder

(10) Patent No.: US 12,029,681 B2
(45) Date of Patent: Jul. 9, 2024

(54) THERAPEUTIC EYE MASK SYSTEM

(71) Applicant: BRUDER HEALTHCARE COMPANY, LLC, Alpharetta, GA (US)

(72) Inventor: Mark H. Bruder, Alpharetta, GA (US)

(73) Assignee: THE HILSINGER COMPANY PARENT, LLC, Mansfield, MA (US)

( * ) Notice: Subject to any disclaimer, the term of this patent is extended or adjusted under 35 U.S.C. 154(b) by 421 days.

(21) Appl. No.: 16/107,200

(22) Filed: Aug. 21, 2018

(65) Prior Publication Data
US 2019/0000666 A1 Jan. 3, 2019

Related U.S. Application Data

(63) Continuation-in-part of application No. 15/443,199, filed on Feb. 27, 2017, now abandoned.
(Continued)

(51) Int. Cl.
A61F 7/02 (2006.01)
A61F 7/00 (2006.01)
(Continued)

(52) U.S. Cl.
CPC .......... A61F 7/02 (2013.01); A61F 13/00063 (2013.01); A61F 13/124 (2013.01);
(Continued)

(58) Field of Classification Search
CPC ................ A61F 7/02; A61F 2007/0211; A61F 2007/0004; A61F 2007/0261; A61F 2007/0263; A61F 13/124; A61F 13/00063
See application file for complete search history.

(56) References Cited

U.S. PATENT DOCUMENTS 2,066,271 A 12/1936 Irwin
2,710,008 A 6/1955 Jensen
(Continued)

FOREIGN PATENT DOCUMENTS

EP 0099748 A1 2/1984
EP 0230387 A2 7/1987
(Continued)

OTHER PUBLICATIONS

International Search Report & Written Opinion for PCT/US2019/046128; dated Jan. 15, 2020; 15 pgs.
(Continued)

Primary Examiner — Catharine L Anderson
Assistant Examiner — Arjuna P Chatrathi
(74) Attorney, Agent, or Firm — Perilla Knox & Hildebrandt LLP

(57) ABSTRACT

A therapeutic mask system for treatment of the eyes, including a mask portion for attachment to the head of a patient and an eye coverage pod that is detachably coupled to the mask portion. The mask portion can include an eye coverage portion having a receiver in which the eye coverage pod is releasably secured. Alternatively, the therapeutic mask system includes a mask strap and the eye coverage pod is directly secured to the mask strap. The eye coverage pod includes material for delivering thermal, moisture and/or medication therapy and treatment to the eye. The therapeutic mask system can also include a heat-transmissive treatment pad positioned between the pod and the eye of the user.

14 Claims, 13 Drawing Sheets

Related U.S. Application Data

(60) Provisional application No. 62/548,774, filed on Aug. 22, 2017, provisional application No. 62/430,430, filed on Dec. 6, 2016, provisional application No. 62/301,999, filed on Mar. 1, 2016.

(51) Int. Cl.
*A61F 13/00* (2024.01)
*A61F 13/12* (2006.01)

(52) U.S. Cl.
CPC .............. *A61F 2007/0004* (2013.01); *A61F 2007/0204* (2013.01); *A61F 2007/0215* (2013.01); *A61F 2007/0219* (2013.01); *A61F 2007/022* (2013.01); *A61F 2007/0223* (2013.01); *A61F 2007/0228* (2013.01); *A61F 2007/023* (2013.01); *A61F 2007/0231* (2013.01); *A61F 2007/0242* (2013.01); *A61F 2007/0261* (2013.01); *A61F 2007/0268* (2013.01)

(56) References Cited

U.S. PATENT DOCUMENTS

| | | |
|---|---|---|
| 2,882,244 A | 4/1959 | Milton |
| 3,008,803 A | 11/1961 | Milton |
| 3,010,789 A | 11/1961 | Milton |
| 3,012,853 A | 12/1961 | Milton |
| 3,013,982 A | 12/1961 | Breck et al. |
| 3,030,181 A | 4/1962 | Milton |
| 3,587,578 A | 6/1971 | Walker |
| 4,000,028 A | 12/1976 | Hoey |
| 4,001,732 A | 1/1977 | Gundry |
| 4,106,478 A | 8/1978 | Higashijima |
| 4,252,119 A | 2/1981 | Coates |
| 4,273,621 A | 6/1981 | Fornoff |
| 4,372,318 A | 2/1983 | Viesturs et al. |
| 4,516,564 A | 5/1985 | Koiso et al. |
| 4,525,410 A | 6/1985 | Hagiwara et al. |
| 4,677,974 A * | 7/1987 | Leonardi .............. A61F 13/124 604/289 |
| 4,775,585 A | 10/1988 | Hagiwara et al. |
| 4,826,497 A | 5/1989 | Marcus et al. |
| 4,882,349 A | 11/1989 | Baglioni |
| 4,897,297 A | 1/1990 | Zafiroglu |
| 4,906,466 A | 3/1990 | Edwards et al. |
| 4,919,648 A | 4/1990 | Sibalis |
| 4,988,053 A | 1/1991 | Choi |
| 5,019,254 A | 5/1991 | Abrevaya et al. |
| 5,028,435 A | 7/1991 | Katz et al. |
| 5,123,900 A | 6/1992 | Wick |
| 5,135,518 A | 8/1992 | Vera |
| 5,179,944 A | 1/1993 | McSymytz |
| 5,300,104 A | 4/1994 | Gaudreault et al. |
| 5,314,005 A | 5/1994 | Dobry |
| RE34,692 E | 8/1994 | Becher |
| 5,366,491 A | 11/1994 | Ingram et al. |
| 5,378,475 A | 1/1995 | Smith et al. |
| 5,409,472 A | 4/1995 | Rawlings et al. |
| 5,413,788 A | 5/1995 | Edwards et al. |
| 5,447,531 A | 9/1995 | Wood |
| 5,584,086 A | 12/1996 | Vanwinkle et al. |
| 5,697,961 A | 12/1997 | Kiamil |
| 5,700,238 A * | 12/1997 | Hyson .............. A61F 13/124 604/303 |
| 5,846,559 A | 12/1998 | Hopp |
| 5,890,487 A | 4/1999 | Kimmel |
| 5,900,258 A | 5/1999 | Engler |
| 5,935,486 A | 8/1999 | Bell et al. |
| 5,948,010 A | 9/1999 | Adamec et al. |
| 5,977,428 A | 11/1999 | Bozigian et al. |
| 5,984,995 A | 11/1999 | White |
| 6,017,606 A | 1/2000 | Sage et al. |
| 6,019,782 A | 2/2000 | Davis et al. |
| 6,045,820 A | 4/2000 | Messier |
| 6,169,223 B1 | 1/2001 | Mahr et al. |
| 6,193,740 B1 * | 2/2001 | Rodriguez .............. A61F 9/04 606/204.15 |
| 6,353,145 B1 | 3/2002 | Church |
| 6,409,746 B1 | 6/2002 | Igaki et al. |
| 6,537,308 B2 | 3/2003 | Burkhart |
| 6,576,004 B2 | 6/2003 | Johnston |
| 6,592,888 B1 | 7/2003 | Jensen et al. |
| 6,617,490 B1 | 9/2003 | Chen et al. |
| 6,641,264 B1 | 11/2003 | Schwebel |
| 6,752,998 B2 | 6/2004 | Verdrel-Lahaxe et al. |
| 6,823,860 B2 | 11/2004 | Igaki et al. |
| 6,874,884 B2 | 4/2005 | Schwebel |
| 7,036,928 B2 | 5/2006 | Schwebel |
| 7,137,965 B2 | 11/2006 | Fischer et al. |
| 7,211,070 B2 | 5/2007 | Soroudi |
| 7,231,922 B2 | 6/2007 | Davison et al. |
| 7,357,500 B2 | 4/2008 | Schwebel |
| 7,513,893 B2 | 4/2009 | Soroudi |
| 7,559,907 B2 | 7/2009 | Krempel et al. |
| 7,601,168 B2 | 10/2009 | Koby et al. |
| 7,652,228 B2 | 1/2010 | Igaki et al. |
| 7,976,573 B2 | 7/2011 | Korb et al. |
| 7,981,147 B2 | 7/2011 | Korb et al. |
| 8,025,689 B2 | 9/2011 | Korb et al. |
| 8,034,092 B2 | 10/2011 | Bruder et al. |
| 8,109,964 B2 * | 2/2012 | Payne .............. A61F 13/124 607/109 |
| 8,114,433 B2 | 2/2012 | Huey et al. |
| 8,202,853 B2 | 6/2012 | Adkins, Jr. |
| 8,235,954 B2 | 8/2012 | Soroudi |
| 8,246,978 B2 | 8/2012 | Kydonieus et al. |
| 8,261,734 B2 | 9/2012 | Dodo |
| 8,319,002 B2 | 11/2012 | Daniels et al. |
| 8,333,793 B2 | 12/2012 | Igaki et al. |
| 8,343,203 B2 | 1/2013 | Ishikawa |
| 8,349,806 B2 | 1/2013 | Brubaker et al. |
| 8,357,189 B2 | 1/2013 | Ugajin et al. |
| 8,409,154 B2 | 4/2013 | Mitra et al. |
| 8,420,882 B2 | 4/2013 | Bruder et al. |
| 8,430,921 B2 | 4/2013 | Wong et al. |
| 8,455,016 B2 | 6/2013 | Maskin |
| 8,506,539 B2 | 8/2013 | Guillon et al. |
| 8,524,973 B2 | 9/2013 | Bruder et al. |
| 8,535,363 B1 | 9/2013 | Lewis |
| 8,617,229 B2 | 12/2013 | Korb et al. |
| 8,636,786 B2 * | 1/2014 | Biser .............. A61F 7/02 607/107 |
| 8,642,831 B2 | 2/2014 | Larsen et al. |
| 8,709,039 B2 | 4/2014 | Humphreys |
| 8,747,888 B2 | 6/2014 | Kydonieus et al. |
| 8,778,301 B2 | 7/2014 | Mamelak et al. |
| 8,784,391 B1 | 7/2014 | Biser |
| 8,795,718 B2 | 8/2014 | Bedard et al. |
| 8,900,626 B2 | 12/2014 | Ogawa et al. |
| 8,906,427 B2 | 12/2014 | Maskin |
| 9,115,078 B2 | 8/2015 | Smith et al. |
| 9,216,028 B2 | 12/2015 | Korb et al. |
| 9,445,939 B2 | 9/2016 | Bruder et al. |
| 9,592,149 B2 | 3/2017 | Hidaka et al. |
| D783,854 S | 4/2017 | Biser et al. |
| 9,642,740 B2 | 5/2017 | Bruder et al. |
| 9,671,134 B2 | 6/2017 | Saita et al. |
| 9,719,977 B2 | 8/2017 | Korb et al. |
| 9,724,230 B2 | 8/2017 | Badawi |
| 9,763,827 B2 | 9/2017 | Kelleher et al. |
| 9,925,087 B2 | 3/2018 | Bruder et al. |
| 9,999,539 B2 | 6/2018 | Johnson |
| 10,105,259 B2 * | 10/2018 | Bruder .............. A61F 7/02 |
| D844,795 S | 4/2019 | Bruder |
| 10,314,346 B2 | 6/2019 | Potnis |
| 10,369,056 B2 | 8/2019 | Paulson |
| D870,906 S | 12/2019 | Bruder |
| D871,598 S | 12/2019 | Bruder |
| 10,500,087 B2 | 12/2019 | Thomas et al. |
| 11,076,983 B2 | 8/2021 | Biser et al. |
| 2001/0009831 A1 | 7/2001 | Schink et al. |
| 2002/0032153 A1 | 3/2002 | Whitehouse |

(56) References Cited

U.S. PATENT DOCUMENTS

| | | | |
|---|---|---|---|
| 2002/0193026 A1 | 12/2002 | Ota et al. | |
| 2003/0055366 A1* | 3/2003 | Chalek | A61F 7/02 602/2 |
| 2005/0022823 A1 | 2/2005 | Davison et al. | |
| 2005/0118383 A1* | 6/2005 | Cargill | A61F 7/02 428/36.1 |
| 2005/0278008 A1* | 12/2005 | Ladmer | A61F 7/02 607/109 |
| 2007/0009583 A1 | 1/2007 | Qvist | |
| 2008/0200885 A1 | 8/2008 | Schwebel | |
| 2008/0251085 A1 | 10/2008 | Schwebel | |
| 2009/0043365 A1 | 2/2009 | Friedland et al. | |
| 2009/0104243 A1 | 4/2009 | Utkhede et al. | |
| 2009/0149925 A1* | 6/2009 | MacDonald | G01N 31/229 607/96 |
| 2009/0175926 A1 | 7/2009 | Adams | |
| 2009/0287282 A1 | 11/2009 | Biser et al. | |
| 2009/0287283 A1* | 11/2009 | Biser | A61F 7/02 607/109 |
| 2010/0106111 A1* | 4/2010 | Schwebel | B32B 7/12 604/294 |
| 2010/0145469 A1 | 6/2010 | Barralet et al. | |
| 2010/0312317 A1* | 12/2010 | Baltazar | A61F 7/02 607/109 |
| 2011/0208279 A1 | 8/2011 | Sanker | |
| 2011/0307041 A1 | 12/2011 | Floyd | |
| 2012/0128763 A1 | 5/2012 | Maskin | |
| 2013/0071322 A1 | 3/2013 | Figuly | |
| 2013/0131613 A1 | 5/2013 | Elkins | |
| 2013/0317459 A1 | 11/2013 | Bruder et al. | |
| 2013/0317460 A1 | 11/2013 | Bruder et al. | |
| 2014/0142667 A1 | 5/2014 | Biser et al. | |
| 2014/0186420 A1 | 7/2014 | Utkhede et al. | |
| 2014/0277303 A1 | 9/2014 | Biser et al. | |
| 2014/0288624 A1 | 9/2014 | Wasko et al. | |
| 2014/0330222 A1* | 11/2014 | Bruder | A61F 7/02 604/290 |
| 2015/0085257 A1* | 3/2015 | Masket | A61B 3/02 351/222 |
| 2015/0088236 A1 | 3/2015 | Bruder et al. | |
| 2015/0182415 A1 | 7/2015 | Olkowski et al. | |
| 2016/0120692 A1 | 5/2016 | Chen | |
| 2016/0206476 A1 | 7/2016 | Robertson et al. | |
| 2017/0049614 A1 | 2/2017 | Paulson | |
| 2017/0216088 A1 | 8/2017 | Johnson | |
| 2017/0252210 A1 | 9/2017 | Bruder | |
| 2017/0266035 A1 | 9/2017 | Kuo | |
| 2017/0266053 A1 | 9/2017 | Rodriguez | |
| 2018/0289531 A1 | 10/2018 | Thomas et al. | |
| 2018/0338864 A1 | 11/2018 | Paulson | |
| 2019/0000666 A1 | 1/2019 | Bruder | |
| 2019/0053940 A1 | 2/2019 | Biser et al. | |
| 2019/0083299 A1 | 3/2019 | Rozanski | |
| 2019/0125579 A1 | 5/2019 | Habib | |
| 2019/0159929 A1 | 5/2019 | Bruder | |
| 2019/0183671 A1 | 6/2019 | Baltazar | |
| 2019/0216639 A1 | 7/2019 | Bruder | |
| 2020/0337893 A1 | 10/2020 | Bruder et al. | |
| 2021/0267793 A1 | 9/2021 | Bruder et al. | |

FOREIGN PATENT DOCUMENTS

| | | |
|---|---|---|
| EP | 0457977 A1 | 11/1991 |
| EP | 0691113 A1 | 1/1996 |
| EP | 1652536 A1 | 5/2006 |
| EP | 1328225 B1 | 3/2010 |
| FR | 2370479 A1 | 6/1978 |
| GB | 1315431 | 5/1973 |
| GB | 1417962 | 12/1975 |
| GB | 2228682 A | 9/1990 |
| GB | 2259858 A | 3/1993 |
| JP | H07112021 A | 5/1995 |
| JP | 2013075023 A | 4/2013 |
| JP | 20170033564 A | 3/2017 |
| WO | 9213576 A1 | 8/1992 |
| WO | 9909920 A1 | 3/1999 |
| WO | 0178797 A1 | 10/2001 |
| WO | 0222060 A1 | 3/2002 |
| WO | 2014143139 A1 | 9/2014 |
| WO | 2017197496 A1 | 11/2017 |

OTHER PUBLICATIONS

Bentonite Definition; Encyclopaedia Britannica; 1 pg; date unknown.
Cerdak Corporation, Home page, online, accessed Jun. 30, 2015 <http://www.cerdak.co.za/Home/>.
Cerdak Corporation, "Products," online, accessed Jun. 30, 2015 <http://www.cerdak.co.za/Products/>.
File History for U.S. Appl. No. 10/341,806.
File History for U.S. Appl. No. 13/291,059.
Healthcare Packaging; date unknown; 3 pages.
Healthcare Packaging; Examining Transdermal Delivery Developments; May 1, 2013; 5 pages.
International Preliminary Examination report for PCT/US01/28908 dated May 27, 2003.
International Search Report for PCT/US01/28908 dated Jan. 24, 2002.
International Search Report for PCT/US13/53221 dated Oct. 17, 2013.
Invitation to Pay Additional Fees for PCT/US2017/019621; dated May 31, 2017; 12 pgs.
Non-Patent Literature cited by EPO in Examination of EP 0691113 May 31, 1995.
Patent Owner Amended Infringement Contentions for U.S. Pat. No. 8,420,882 filed Jun. 24, 2014.
Supplementary European Search Report for EP Application 01 97 3065 dated Aug. 1, 2006.
"Technology helps heal chronic wounds," Mraz, S. 2011, Machine Design, online, 5 pp., accessed Jun. 30, 2015. <http://machinedesign.com/medical/technology-helps-heal-chronic-wounds>.
Treatment Restore Gland Function; LipiFlow; http://tearscience.com/en/; 2 pgs; date unknown.
U.S. Appl. No. 60/232,826, filed Sep. 15, 2000.
U.S. Appl. No. 60/349,335, filed Jan. 14, 2002.
Zmedica—QuikClot Sport Silver; date unknown; 1 page.
Wikipedia: Antimicrobials, p. 4, essential oils, citing references 24 (1998); 25 (2003); https://en.wikipedia.org/w/index.php?title=Antimicrobial&oldid=1086603183 (Year:2022).

* cited by examiner

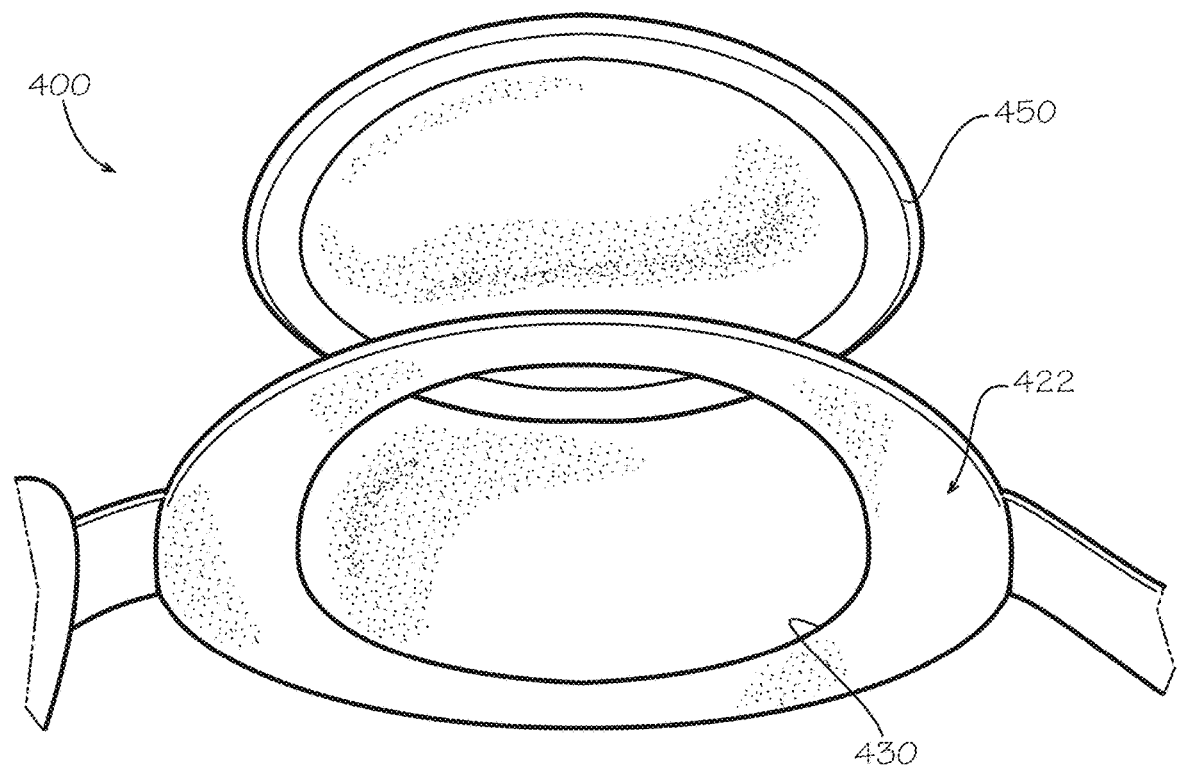
FIG. 14
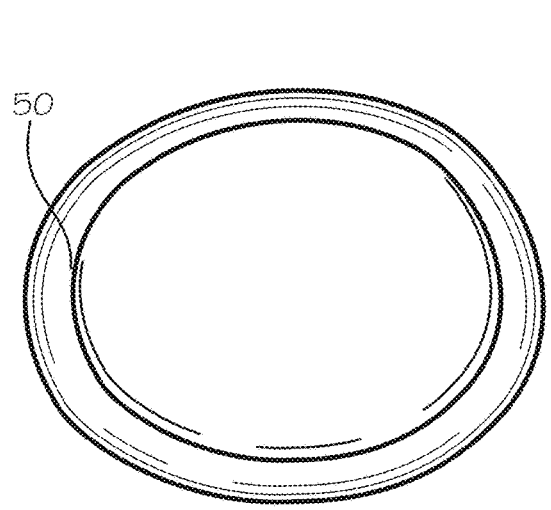 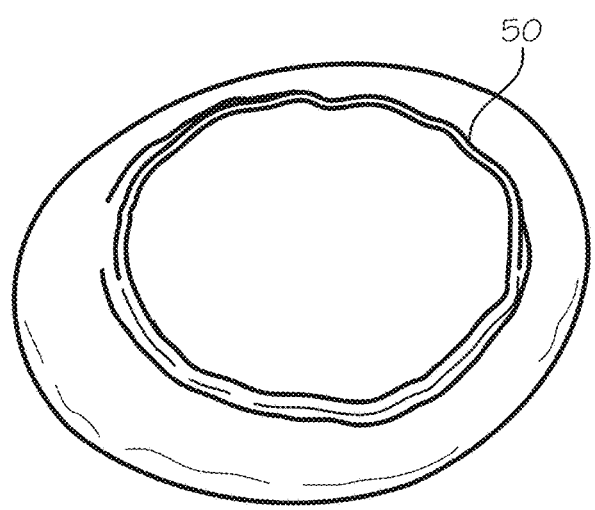
FIG. 15 FIG. 16

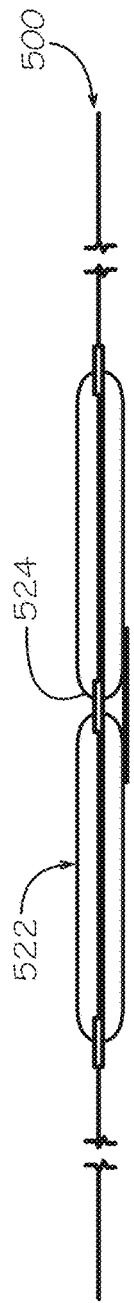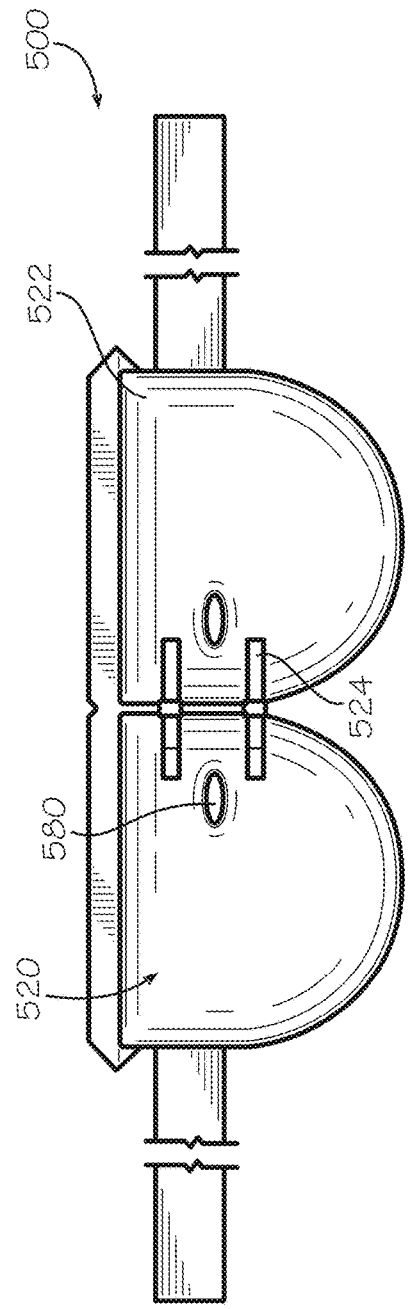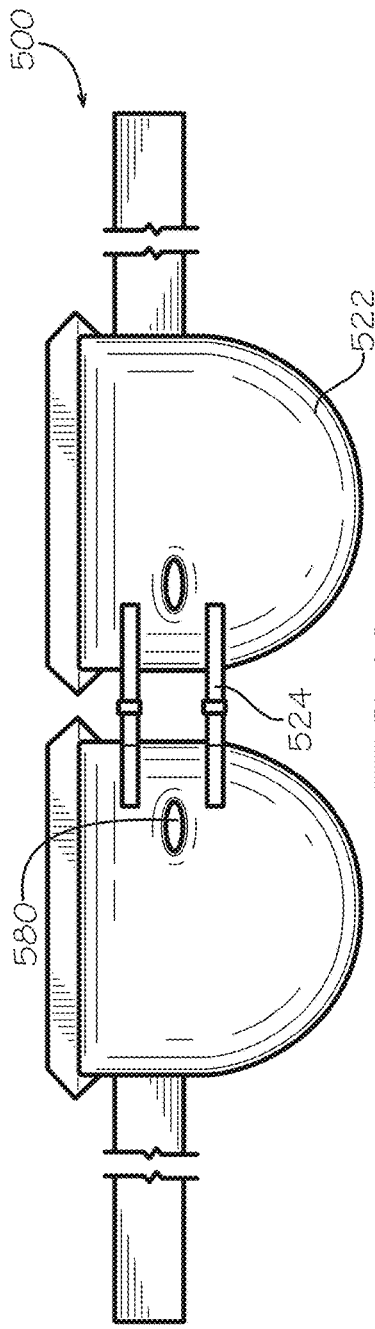

THERAPEUTIC EYE MASK SYSTEM

CROSS-REFERENCE TO RELATED APPLICATIONS

This application is a continuation-in-part of U.S. Non-Provisional patent application Ser. No. 15/443,199 filed Feb. 27, 2017, which claims priority to U.S. Provisional Patent Application Ser. No. 62/301,999 filed Mar. 1, 2016 and U.S. Provisional Patent Application Ser. No. 62/430,430 filed Dec. 6, 2016; this application also claims priority to U.S. Provisional Patent Application Ser. No. 62/548,774 filed Aug. 22, 2017, all of which are hereby incorporated herein by reference in its entirety.

TECHNICAL FIELD

The present invention relates generally to the field of ophthalmic medical therapy or palliative care of the eye. More particularly, the present invention relates to a mask or compress for thermal treatment and/or delivery of medication to the eyes, sinus and facial areas of a subject or patient.

BACKGROUND

Various conditions of the eye may require medical or palliative care. For example, blepharitis is a common and ongoing condition where the eyelids become inflamed (swollen), with oily particles and bacteria coating the eyelid margin near the base of the eyelashes. This condition causes irritation, itchiness, redness, dry eye and stinging or burning of the eyes. While the underlying causes of blepharitis are not completely understood, it can be associated with a bacterial eye infection, symptoms of dry eyes or certain types of skin conditions such as acne rosacea. Anterior blepharitis affects the outside of the eyelid where the eyelashes are attached. This can be caused by bacterial (or sometimes viral) infection. If left untreated, anterior blepharitis can lead to thickened and inward-turned or outward-turned eyelids and even vision problems from in-turned eyelashes damaging the cornea. Posterior blepharitis is a condition that results from a dysfunction of the eye's tiny oil glands (meibomian glands) in the eyelids at the base of the eyelashes. When meibomian glands become clogged from posterior blepharitis, it can cause a stye or chalazion to form. Posterior blepharitis can also lead to thickened eyelid margins and crusty eyelids.

An estimated 40.9 million people in the United States aged 18 or older wear contact lenses. The International Workshop on Contact Lens Discomfort, published in 2013, put forth dryness of the eyes as a primary reason for contact lens intolerance. When a contact lens is placed on the eye, the tear film structure becomes altered resulting in a pre-lens thinned lipid layer and a post-lens thinned aqueous layer. As a result of this disruption from the contact lens, the tear film tends to have an increased rate of evaporation leading to poor wetting on the surface of the contact lens and inadequate lubrication on the surface of the eye. This is further exacerbated if the patient has an already unstable lipid layer due to the presence of meibomian gland dysfunction (MGD). MGD is considered by many to be the leading cause of dry eye disease throughout the world and is a chronic and progressive condition that can contribute to a poor quality lipid layer and lead to contact lens discomfort. Contact lens wearers often report dry eye symptoms and show signs of MGD including gland atrophy, thinned lipid layer, and increased tear film instability. It has been shown that in many patients with intolerance to contact lenses, MGD has been observed. Therefore, treatment of MGD may support the functioning of the meibomian glands and lead to improvement in patient contact lens comfort.

Hygienic home treatment of such ocular disorders can be a two-step process. First, the patient softens the debris and scurf that accumulates around the eye. The debris can be softened by applying a warm compress, diluted baby shampoo, or a specialized liquid solution to the eyelid margin. This first step is intended to prepare the debris for removal while preventing further irritation to the eye. Second, the patient can attempt to remove the debris by physically scrubbing the eyelid margin, the base of the eyelashes, and the pores of the meibomian glands. This scrubbing is routinely attempted with either a generic cotton swab, a fingertip, or a scrub pad placed over the fingertip and applied against the eye. By cleaning debris and scurf free from the base of the eyelashes and unclogging the pores of the meibomian glands, the patient may improve the overall health of the eyelid margin; thereby reducing irritation, burning, and other symptoms related to the disorder.

Thermal therapy can also be used for medical or palliative care of a human or animal subject or patient, for example by delivering moist heat or cold to the eye region. In example applications, thermal therapy can be used to unblock glands in the eye to help treat dry eye. Moist heat may also be used to help reduce elevated intraocular pressure to either treat or help prevent open-angle glaucoma. Delivery of medications to the eyes, such as for treatment of blepharitis may be enhanced by application of thermal therapy in combination with the medication. Applying heat to the inner eyelid may also help safely remove gland obstructions and stagnant gland content.

Many currently known eye treatment masks are not designed to securely fit the eye, causing issues in some forms of therapeutic treatment. For example, when a patient uses a continuous positive airway pressure (CPAP) machine for treatment of sleep apnea, air can sometimes blowback from the mask of the CPAP machine into the user's eyes, causing dryness of the eyes. Known eye masks and eye compresses may not fit securely to the eye and have not been found entirely successful in protecting the eyes from this blow-back dryness.

Needs exist for improvements to ophthalmic medical therapy or palliative care of the eye. It is to the provision improved therapeutic eye mask system and treatment methods meeting these and other needs that the present invention is primarily directed.

SUMMARY

In example embodiments, the present invention provides a therapeutic mask system for treatment of the eyes, including a mask portion for attachment to the head of a patient and an eye coverage pod that is detachably coupled to the mask portion. The mask portion can include an eye coverage portion comprising a receiver in which the pod is releasably secured. The pods can also be directly secured to a mask strap. The pod includes material for delivering thermal, moisture and/or medication therapy and treatment to the eye. The system can also include a heat-transmissive treatment pad positioned between the pod and the eye of the user.

In example embodiments of the invention, the therapeutic device includes pods having a granular fill material such as a hydrophilic zeolite or molecular sieve material, optionally loaded with at least one metallic or other antimicrobial agent, such as for example a silver, copper, copper oxide, gold, magnesium oxide, aluminum oxide, titanium dioxide, zinc oxide, cobalt, nickel, zirconium, molybdenum, tin, lead and/or other metals, metal oxides, metal ions, metal particles or nanoparticles, and alloys, mixtures or combinations thereof. In example embodiments, the antimicrobial agent is retained in the therapeutic device over multiple uses.

In another aspect, the invention relates to an eye mask article or compress system comprising at least one eye coverage portion for application to at least one eye. The article includes a mask with at least one eye coverage portion for application to the at least one eye. The mask includes at least one indented pocket positioned to align with the at least one eye. The mask also includes at least one thermal treatment delivery pod detachably secured within the at least one indented pocket. The at least one pod includes material for delivering moist heat therapy and treatment to the at least one eye. The mask optionally further comprises medicament dispensed toward the at least one eye by the at least one pod.

In still another aspect of the invention, the therapeutic device includes a mask body configured for attachment to a patient and at least one treatment pod comprising a loose, granular fill material contained within an outer shell. The at least one treatment pod is releasably coupled to the mask body.

In still another aspect of the invention, the ophthalmic therapy device comprises at least one therapy pod configured to cover the eye of the user and a sheet shaped to conform to the eye area of a patient. The sheet is impregnated with medication. The sheet is held between the at least one therapy pod and the eye. The therapy pod releases heat toward the eye and the medication is expelled from the sheet towards the eye.

In still another aspect, the invention relates to a method of treating patient's eyes comprising removably attaching two pods to a therapeutic mask and applying the mask to an eye area of the patient. The pods comprise a heat delivery material.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of preferred embodiments of the invention, and are not restrictive of the invention, as claimed.

BRIEF DESCRIPTION OF THE DRAWINGS

FIG. 14 shows a detailed exploded view of the therapeutic eye mask system of FIG. 13.

FIG. 15 shows a detachable pod for use in a therapeutic eye mask according to an example embodiment of the invention.

FIG. 16 shows a detachable pod according to another example embodiment of the present invention.

FIG. 21 is a side view of a therapeutic eye mask system according to another example embodiment of the invention.

FIG. 22 shows a front view of the therapeutic eye mask system of FIG. 21.

FIG. 23 shows an alternative configuration of the therapeutic eye mask system of FIG. 22.

DETAILED DESCRIPTION OF EXAMPLE EMBODIMENTS

Figure 1:
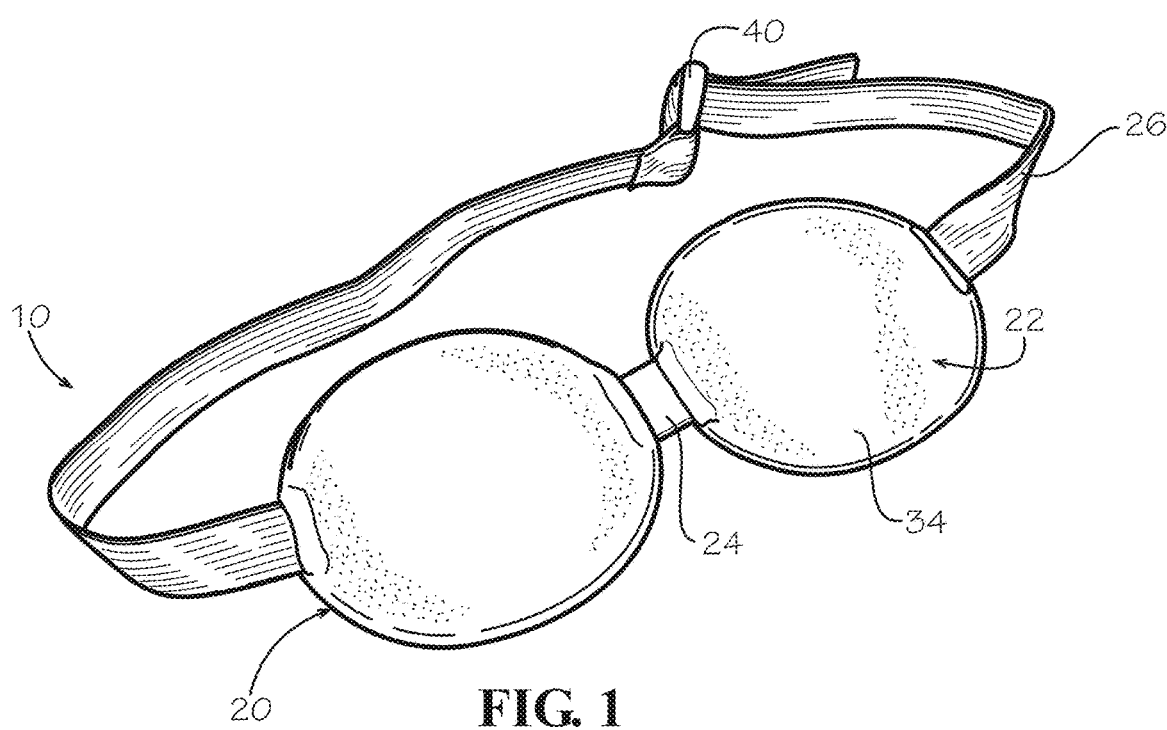
FIG. 1 is a perspective view of a therapeutic eye mask system according to an example embodiment of the invention.
Figure 2:
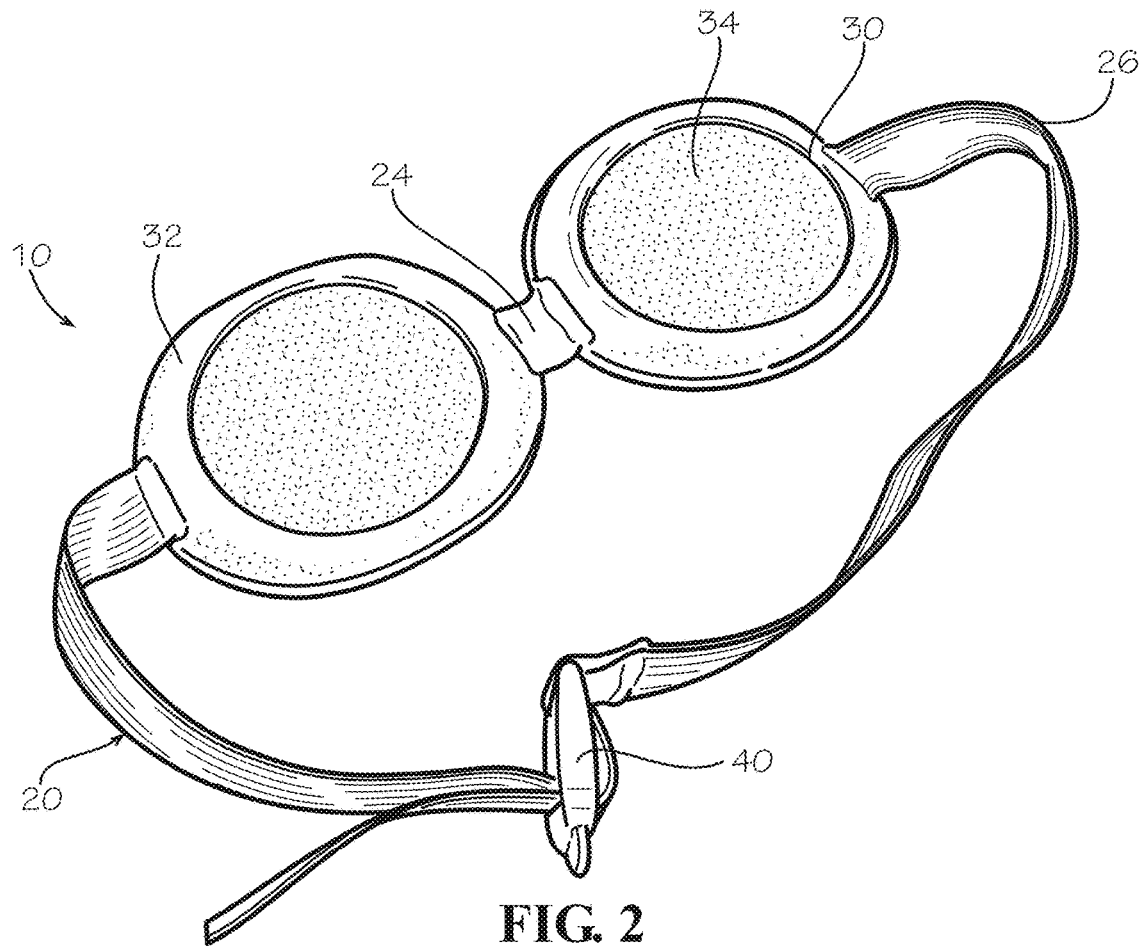
FIG. 2 shows a back view of the therapeutic eye mask system depicted in FIG. 1.
Figure 3:
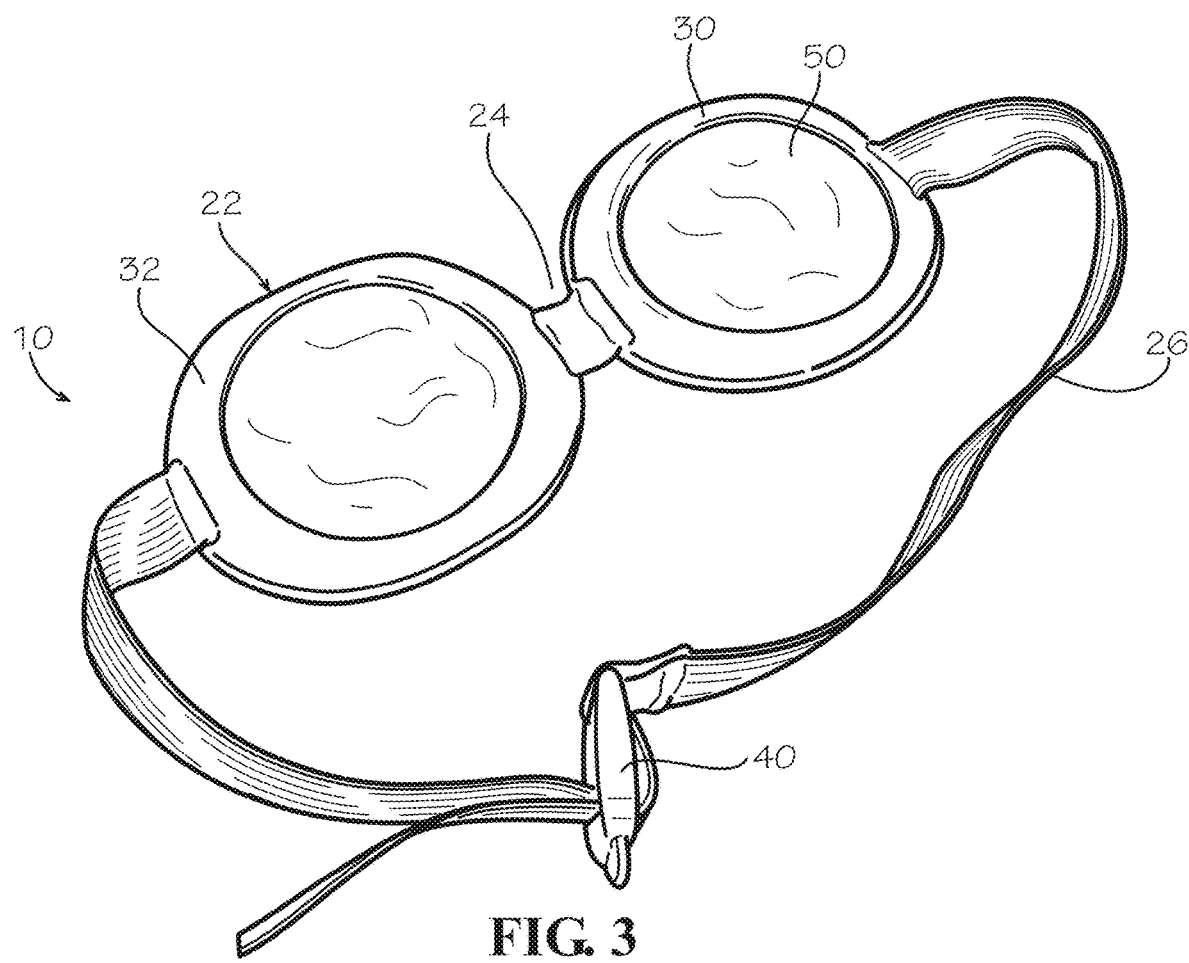
FIG. 3 shows the therapeutic eye mask system depicted in FIG. 2 including detachable pods.
Figure 4A:
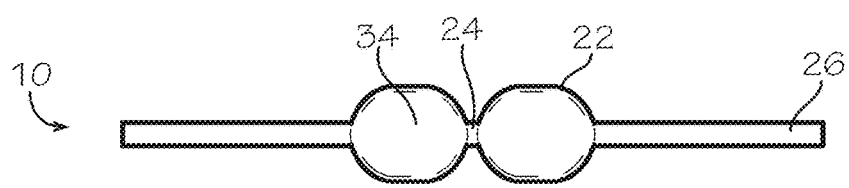
FIGS. 4A-C show a front, back and side view of the therapeutic eye mask system of FIG. 1.
Figure 4B:
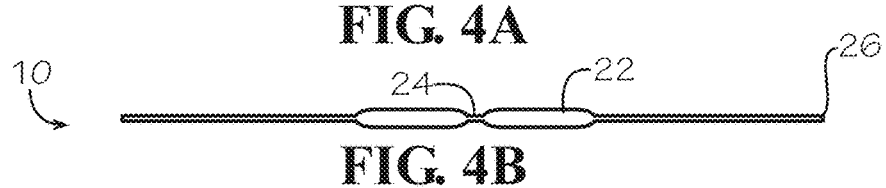
Figure 4C:
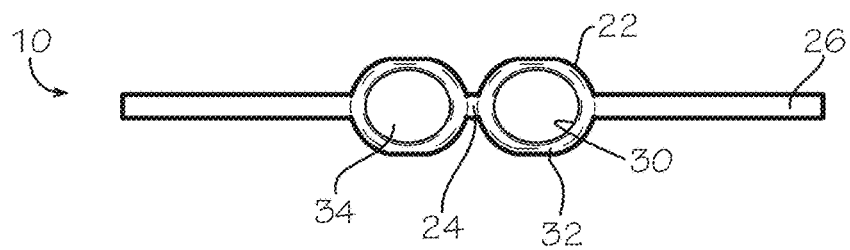
Figure 5:
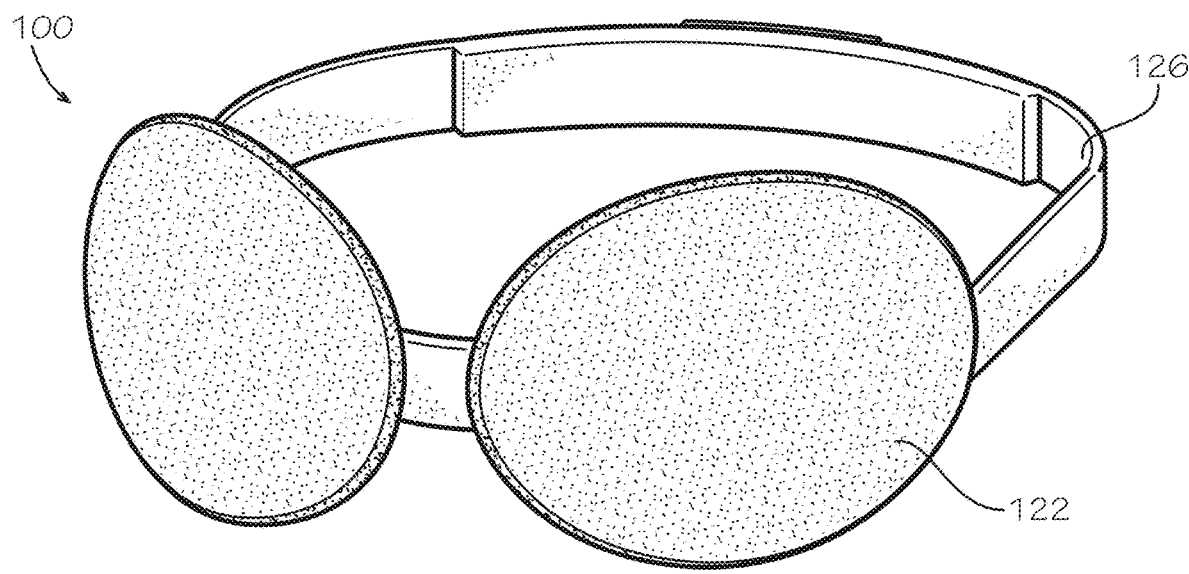
FIG. 5 is a perspective view of a therapeutic eye mask system according to another example embodiment of the invention.
Figure 6:
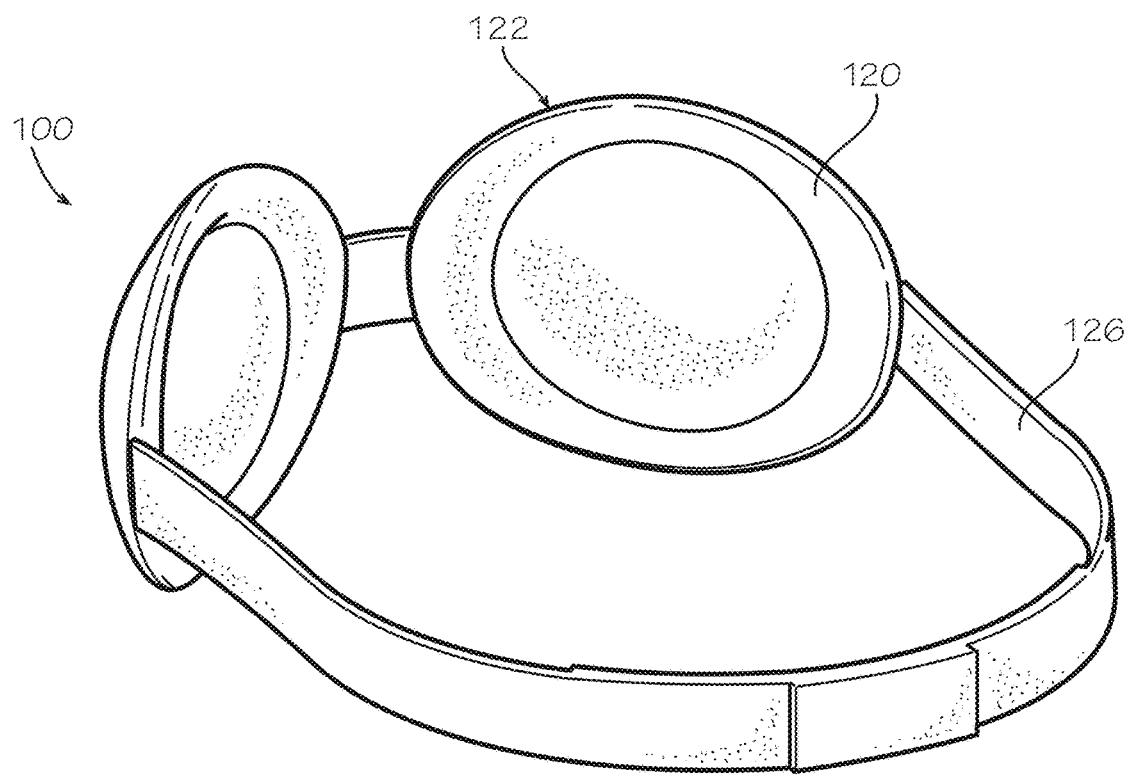
FIG. 6 shows a back view of the therapeutic eye mask system of FIG. 5.
Figure 7A:
FIGS. 7A-C show a front, back and side view of an eye mask portion for use in a therapeutic eye mask system according to another example embodiment of the invention.
Figure 7B:
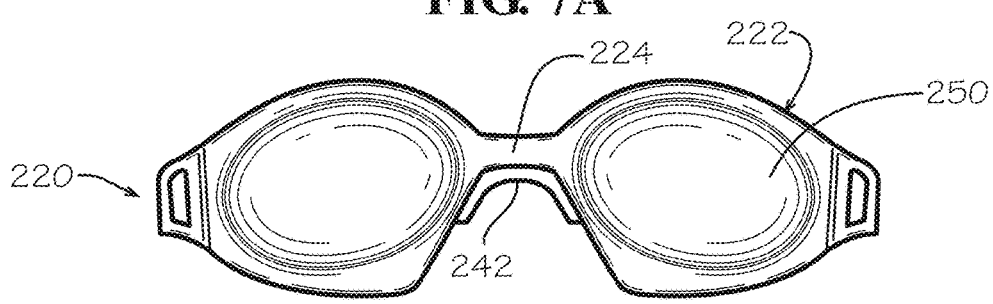
Figure 7C:
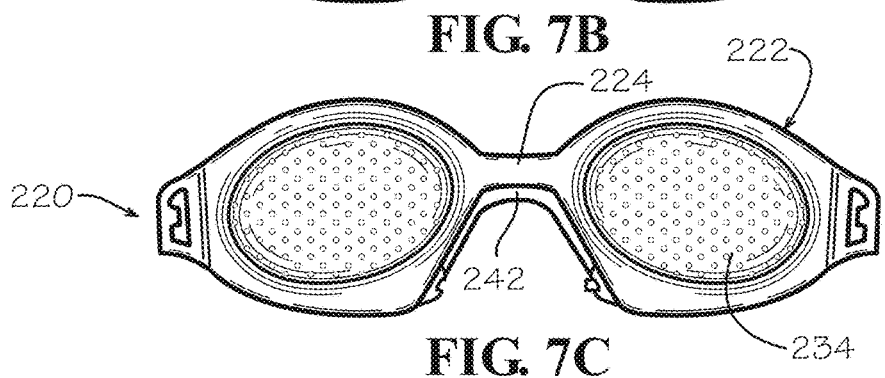
Figure 8A:
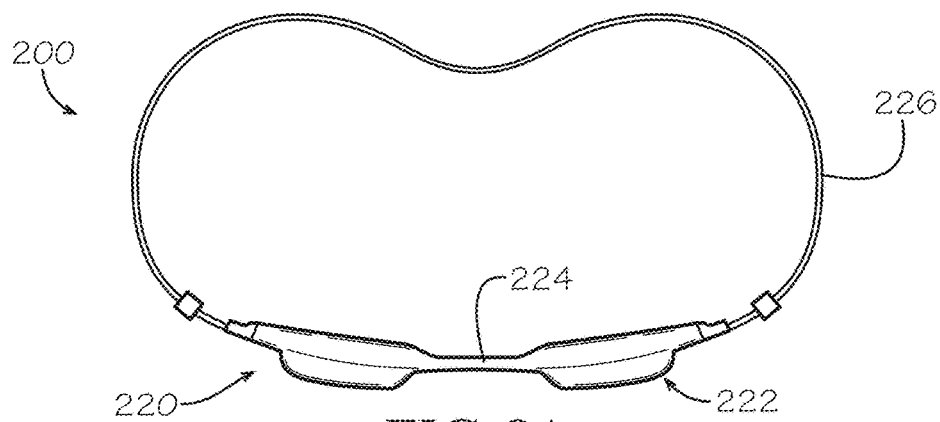
FIGS. 8A-C show a front, top and side views of a therapeutic eye mask system with the eye mask portion of FIGS. 7A-C.
Figure 8B:
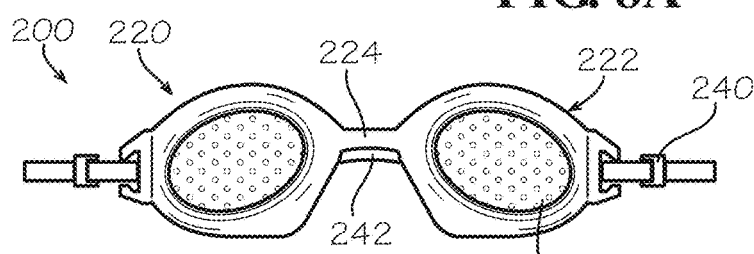
Figure 8C:
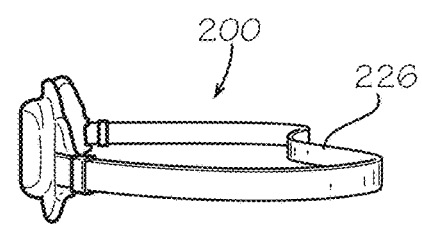

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-23 show a therapeutic eye mask system according to example embodiments of the present invention. The therapeutic eye mask system 10, shown in FIGS. 1-4, generally includes an eye mask 20 and at least one detachable therapy pod 50. The eye mask 20 can include two separate eye coverage portions 22 connected by a nose bridge 24 and a securing strap 26. The mask 20 is configured to be worn on the head of a human patient with one of the eye coverage portions 22 positioned over each eye of the patient. In example embodiments, the securing strap 26 is positioned around the user's head to hold the eye coverage portions 20 against the eyes of the user.

In example embodiments, the mask 20 can have a monolithic uniform construction or may be separate pieces fastened together, for example by stitching, adhesive, fasteners or other attachment means. In example embodiments, the mask 20 is constructed of a lightweight and durable material. The mask 20 can be made of a soft and flexible material, for example, foam or polyester. It can be constructed of perforated thermoformed foam to improve breathability. The mask 20 can be constructed from laminated foam or soft-flexible, open-cell foam with polyester fabric. In particular examples, the mask 20 is constructed from a 2 lb./ft$^3$, ⅜" thick polyether polyurethane foam, flame laminated to matte black polyester fiber interlock fabric on both sides. Alternatively, the mask 20 is constructed from polyester, rayon, spandex, silk or other natural and/or synthetic fabrics or materials. The mask material can optionally be selected to have insulative or heat-transmissive properties to affect the temperature transferred from the mask to the patient's eyes, ensuring safety. The material may optionally be washable for reuse, or alternatively can be a single-use disposable product. In example embodiments, the mask 20 may be constructed of a material containing nanobeads comprising an antimicrobial metal.

The mask 20 depicted in FIGS. 1-4 includes two eye coverage portions 22. The eye coverage portions 22 are designed to be independent structures such that each can independently conform to the respective eye region of the patient. The eye coverage portions 22 can each include a receiver 30 for holding a detachable therapeutic pod 50. The receivers 30 are configured to hold the pods 50 in position over the patient's eyes when the mask 20 is worn. In example embodiments, the receivers 30 are permanently-formed indents or pockets in the eye coverage portion 22. For example, the indents or pockets can be positioned on the side of the mask that directly faces the eyes of the patient when worn. In use, two removable pods 50 are received in the mask 20, one within each of the receivers 30. Each eye coverage portion 22 can optionally include an eye cushion 32 and an eye cover 34. The eye cushion 32 is configured to surround the receiver 30 and provide padding on a portion of the mask 20 that abuts the users face when worn. The eye cover 34 is configured to cover the outside of the eye coverage portion 22. In alternative embodiments, the mask 20 does not include an eye cover 34 and the eye coverage portion 22 is formed from a circular frame that is open when a detachable pod 50 is not in the receiver 30. The eye coverage portions 22 can be a substantially round shape as depicted in FIGS. 1-4 or can be an oval, elliptical, polygonal, angled or another non-round shape.

The eye coverage portions 22 can be connected by a nose bridge 24 and a securing strap 26. The nose bridge 24 can be formed from a flexible and/or elastic material that allows the nose bridge to fit the face shape of a variety of users. In alternate embodiments, the nose bridge 24 is adjustable. In the depicted embodiments, the securing strap 26 is formed from a strap extending between the eye coverage portions 22. The securing strap 26 can include an adjustment mechanism 40 that allows the user to adjust the length of the strap. In alternate embodiments of the eye mask 100, depicted in FIGS. 5 and 6, the securing strap 126 is formed from two straps, each coupled at a first end to an eye coverage portion 122. The second end of each securing strap 126 is configured to be removably coupled to the other securing strap. The attachment mechanism can include snaps, ties, hook-and-loop fasteners or other releasable attachment mechanisms. The nose bridge 24 and securing strap 26 are configured so that the eye mask 20 can be one size to fit all or most users. Alternatively, the eye mask 10 can be produced in different sizes. The securing strap can also include a comfort wrap (not pictured). In alternate embodiments, the mask 20 can include dual supports to fit over the ears in place of the securing strap 26.

In other embodiments, the mask portion 220 of the therapeutic eye mask system 200 is shaped similar to swimming goggles. The eye coverage portions 222 have a teardrop shape with the top and bottom having a curved shape and the side adjacent the nose bridge being straight so as to follow the angle of the nose. The detachable pods 250 have a generally oval shape and are angled relative to the nose bridge 224. The nose bridge 224 can include a padded portion 242 to provide comfort when worn. The eye covers 234 can be perforated for breathability. The securing strap 226 of the depicted embodiment includes two adjustment mechanisms 240, one adjacent to each of the eye coverage portions 222.

Figure 9:
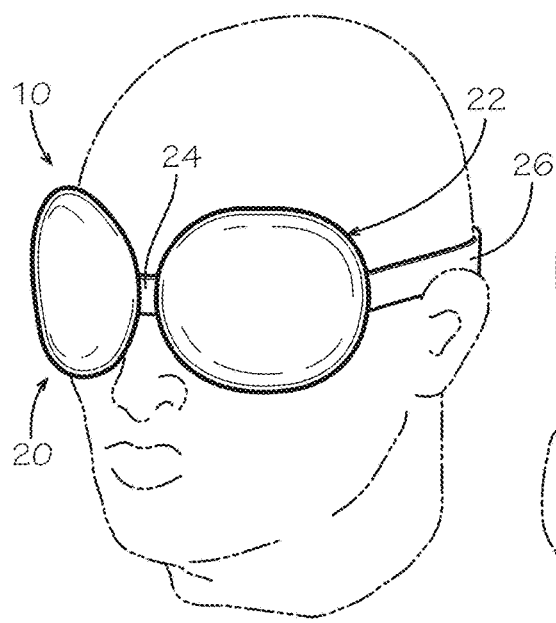
FIG. 9 shows the therapeutic eye mask of FIG. 1 worn by a human patient.
Figure 10:
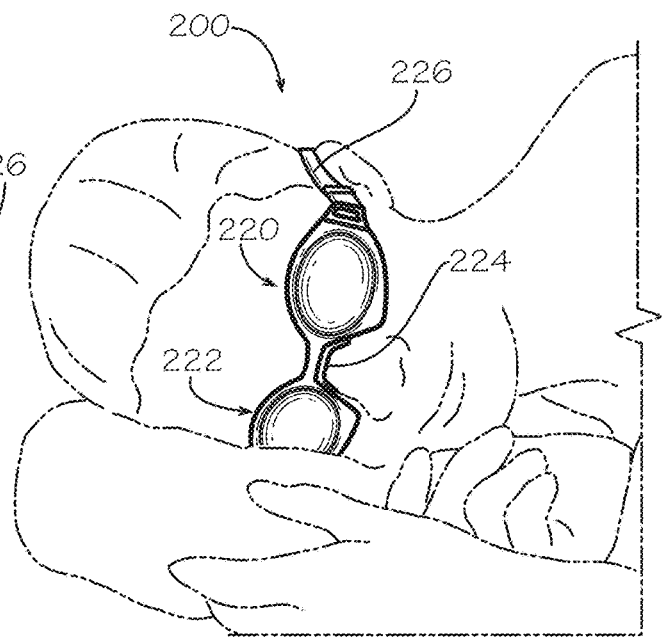
FIG. 10 shows the therapeutic eye mask of FIGS. 8A-C worn by a human patient.
Figure 11A:
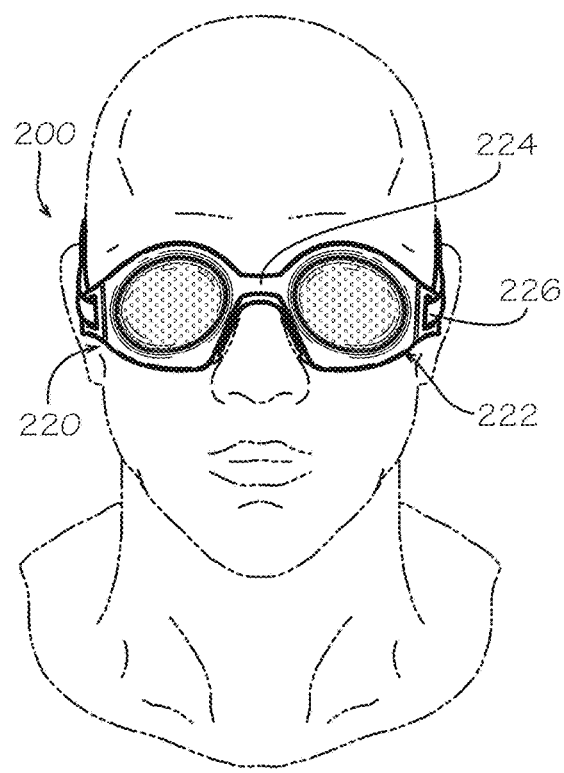
FIGS. 11A-B show the therapeutic eye mask of FIGS. 8A-C worn by a human patient.
Figure 11B:
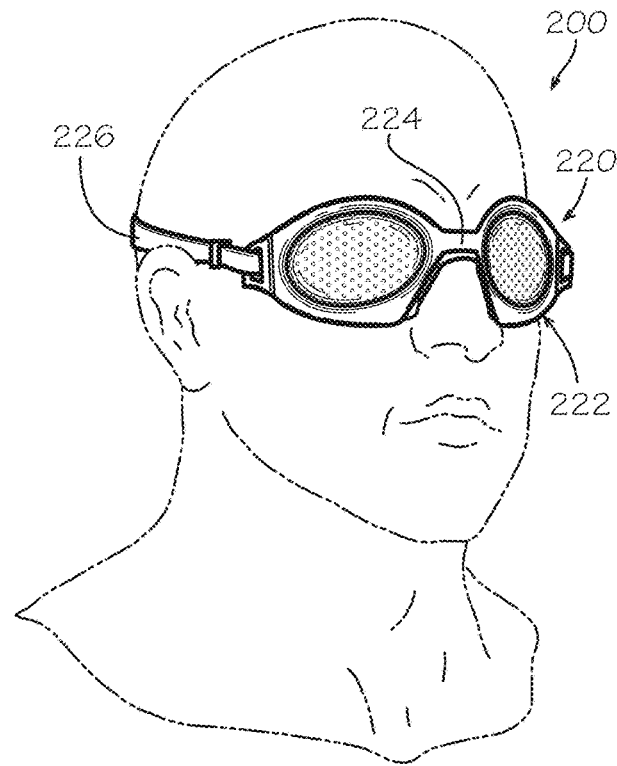

The mask 20, 220 portion of the therapeutic eye mask system 10, 200 is designed to fit securely to the patient's eye region with an eye coverage portion 22, 222 over each eye, the nose bridge 24, 224 positioned across the patient's nose and the securing strap 26, 226 extending around the back of the patient's head, as shown in FIGS. 9-11. The eye mask 20, 220 is designed such that it can be safe and comfortable to wear while sleeping, as shown in FIG. 10. The secure fit can also prevent air from being blown into the eye while the mask is being worn, for example when worn in combination with a CPAP machine. In example embodiments, the dual eye coverage portion design allows full conformance within the eye socket. The design also optionally allows heat and moist therapy to reach the sinuses to help relieve sinus pressure.

As discussed above, the eye coverage portions 22 of the mask 20 each include receivers configured to releasably secure a therapy pod 50. In example embodiments, the pods 50 have a soft outer shell construction that is able to contain a fill material capable of delivering therapy treatment, for example, moist heat and cold treatments. The outer shell of the pods 50 can be formed of fabric, non-wovens or other natural or synthetic materials, and is preferably thermally and moisture transmissive, to allow heat and/or moisture to pass through the shell to and from the fill material. Example fill materials include hydrophilic zeolite granules or particles, and optionally silver or other antimicrobial treatments, and/or other materials. The fill material can be loosely contained and held within the pod 50 such that each pod will conform to the eye area of the patient when worn. Alternatively, a liquid or gel fill material can be used. The pods 50 can be designed for single use or can be washable and re-usable.

In example embodiments, the fill material contained within the pods comprises a synthetic porous crystalline granular aluminosilicate zeolite, for example, a hydrophilic natural or synthetic zeolite, also referred to as a molecular sieve material, or other substances with similar properties. The fill material may further comprise other inert additives and physical matrices without affecting the antimicrobial and hydrous efficacies of the fill. The hydrophilic zeolite granules or beads are configured to repeatedly absorb and release moisture without substantially changing shape or form. Optionally, the pods comprise a granular fill material such as activated alumina, silica gel, bentonite or hydrophilic zeolite or molecular sieve material. In alternate embodiments, the pods comprise capsules or packets of non-granular material (e.g., gel, liquid), powder, or other materials. The pods or granules contained in the pods optionally also contain a metallic or other antimicrobial agent, such as for example a silver, copper, copper oxide, gold, magnesium oxide, aluminum oxide, titanium dioxide, zinc oxide, cobalt, nickel, zirconium, molybdenum, tin, lead and/or other metals, metal oxides, metal ions, metal particles or nanoparticles, and alloys, mixtures or combinations thereof deposited therein. For example, silver or another metal loading of the fill may be attained by the process of ion-exchange. In this process, a solution containing atomic silver or a composition of silver bathes or is passed through a bed of the fill granules. An ion-exchange column method may be performed in which an aqueous solution containing atomic silver or a composition of silver may be passed through a column bed of the fill granules, and the eluted solution may again be passed through the bed or may receive additional silver and then be again passed through the bed.

Various ion-exchange schedules as known in the art may be applied to produce retention of the silver or other metals in the fill material of the pods. For example, the final content by weight of an atomic silver or silver composition, or other metals or antimicrobial agents, may be as high as twenty percent of the final loaded fill granules. In example embodiments, the loaded fill granules produced by ion-exchange will exhibit high retention of the silver or other metals even under subsequent exposure to fluids and microwave irradiation. The fill granules may comprise a blend of both metals loaded and unloaded (i.e., not containing metal) zeolite or other substance(s) retaining silver or other metals. The presence of the atomic silver or other metals preferably will not interfere with the useful properties of the fill granules such as the moisture desorption and adsorption properties which may be desirable in the use of the eye mask or compress system. The inherent hydrophilic nature of example forms of zeolite fill materials provides that substantial water content is available therein by absorption from the atmosphere. The water so absorbed may be sufficient for moist heat delivery applications, or may be supplemented by manually added water, for providing a microwave responsive water content of the eye mask or compress system. The compositions of silver or other metals used may include but are not limited to, metal compounds, and metal salts such as silver chloride and silver nitrate.

The presence of the silver or other metals within the fill granules optionally contained in the pods of the invention provides anti-microbial properties to the therapeutic eye mask system. The ion-exchange loaded fill granules will preferably retain the silver or other metals despite microwave heating as may be required in the use of the eye mask or compress system. Further, the retention of the silver or other metals within the fill granules provides assured antimicrobial performance in a reusable and potentially washable, if so desired, moist heat therapy compress. In other embodiments, the silver or other metals are incorporated into the cover material of the pods, the eye coverage portions, and/or other portions of the eye mask system, in addition to or instead of the fill granules. Alternatively, one or more non-metal antimicrobial materials and/or medications may optionally be incorporated into the fill material, the pods, the eye coverage portions, and/or other portions of the eye mask system.

Figure 12:
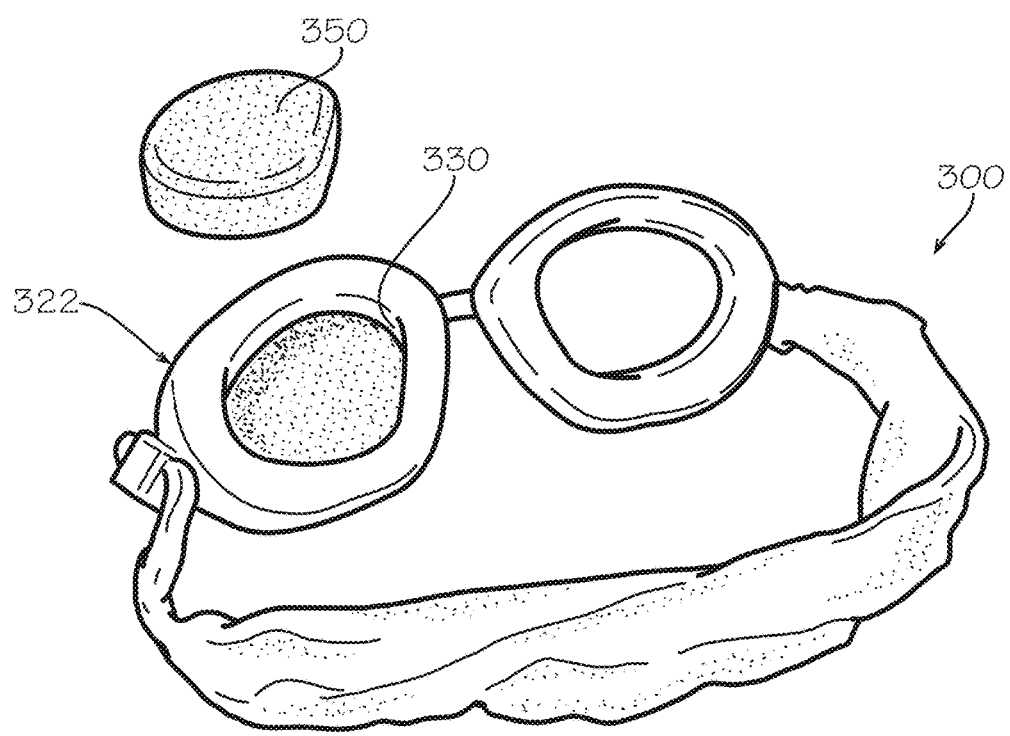
FIG. 12 shows a therapeutic eye mask system according to another example embodiment of the invention.
Figure 17:
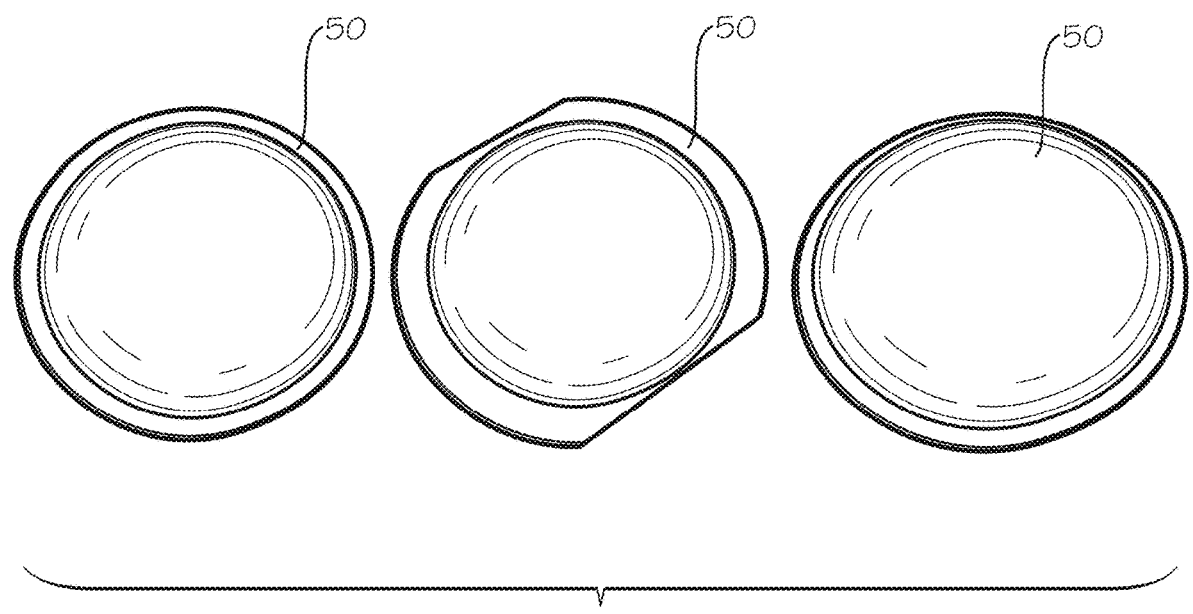
FIG. 17 shows detachable pods of varying shapes according to further example embodiments of the invention.
Figure 18:
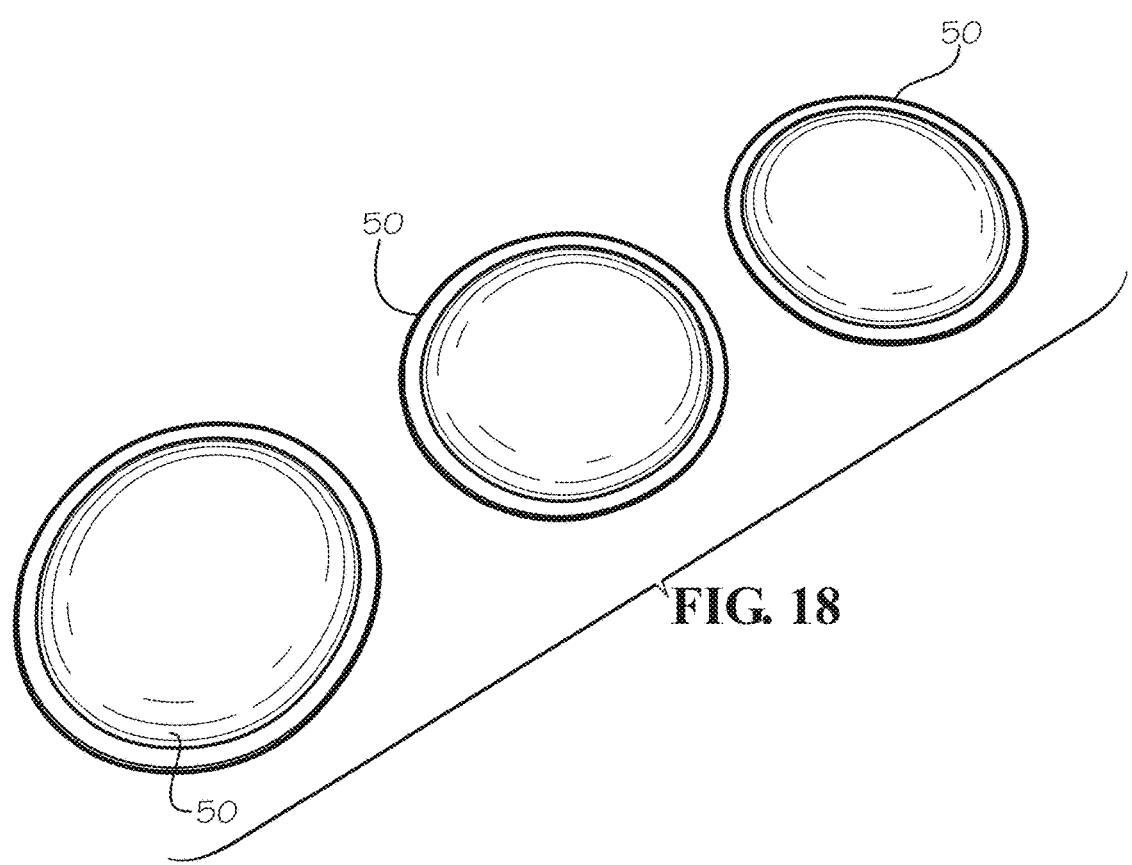
FIG. 18 shows detachable pods of varying sizes according to example embodiments of the invention.

In example embodiments of the therapeutic eye mask system 300, the pods 350 are push-fitted into the receivers 330 in each eye coverage portion 322, as shown in FIG. 12. The pods 350 can be detachably secured within the receivers 330 through the use of an attachment mechanism, for example, a hook-and-loop fastener material secured to both the pods and the receivers, by friction fit, or otherwise. Alternatively, the pods 350 are secured with a positive lock, clip, or a rigid snap. In other embodiments of the therapeutic eye mask system 400, the pods 450 can be slid into the receivers 430 through an opening in the top of the eye coverage portion 422, as shown in FIG. 14. The pods 50 may be round so that they are self-orienting when attached or inserted into the mask, or can be oval, elliptical, polygonal, angled or another non-round shape, as shown in FIG. 17. The pods can be provided in one or more different colors, for example, color coded based on their function. For example, a pod for moist heat treatment may be red and a pod for cool treatment may be blue. The pods 50 can also be provided in different sizes, as shown in FIG. 18. In example embodiments, the material and configuration of the mask form a seal against the wearer's face surrounding the eye area to prevent external airflow from drying the wearer's eyes or drying the pods or medication components positioned within the mask during use.

In use, the entire mask with the pods attached can be heated or cooled prior to use to provide therapy. The mask can be placed in the microwave to be heated or in the freezer to be cooled. Alternatively, the pods alone can be heated or cooled detached from the mask, then placed in the mask when they reach the desired temperature for treatment.

Additionally, various medicaments can be applied and used with respect to the pods. For example, one or more ophthalmic medications can be infused or injected into the formulation in the pods. Examples of medicants or therapeutic materials capable of delivery using the therapeutic device according to example forms of the invention include a jojoba formulation for treatment of the symptoms of dry eye, steroids such as clobetasol propionate, betamethasone dipropionate, amcinonide or loteprednol etabonate for treatments of diseases of the eyelid, such as chatazion, blepharitis or meibomian gland dysfunction. Medicants may also comprise a dietary or nutritional supplement composition comprising an effective amount of omega-3 fatty acids for treatment of dry eye or meibomianitis. Medicants may also comprise tetracycline, corticosteroids, androgens or androgen analogues. The medicant can also comprise a topical treatment to elevate the side effects of chemotherapy, including eyelash loss.

Figure 13:
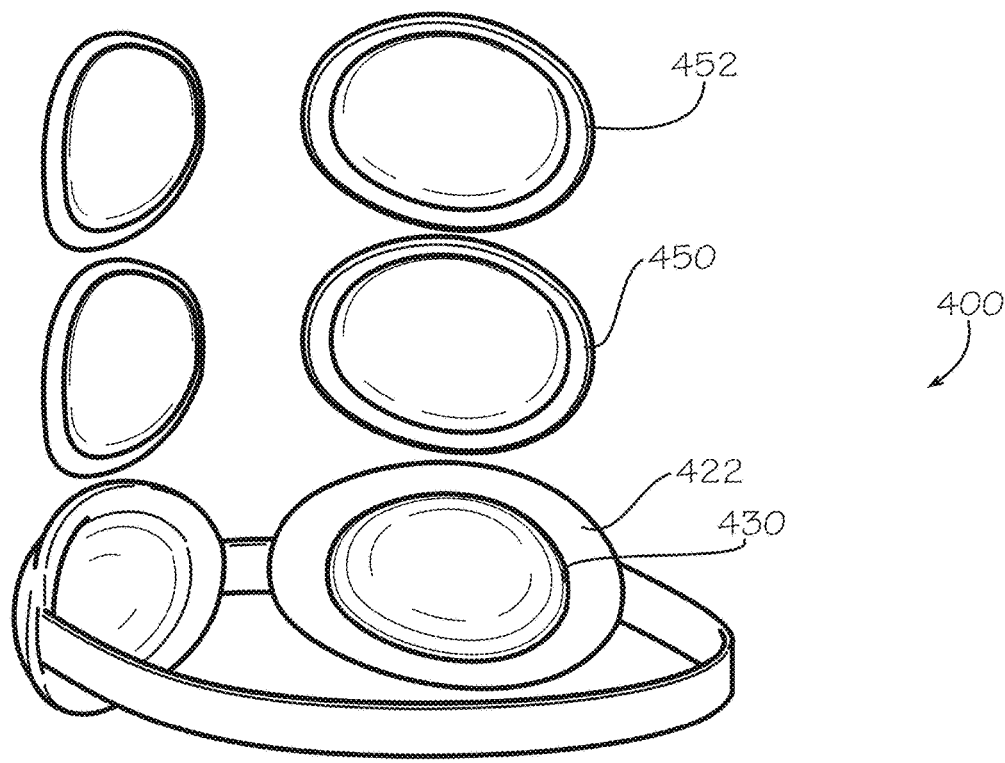
FIG. 13 is an exploded view of a therapeutic eye mask system according to another example embodiment of the invention, having interchangeable pods.

In alternative embodiments, the therapeutic eye mask system 400 may be combined with a heat-transmissive pad or lid scrub or disc 452 that is applied to the skin surface on the eyelid and around the eye, as shown in FIG. 13. In example embodiments, the pad or disc is constructed of a non-woven material and optionally a material that can be RF or thermally sealed to hold an antibacterial or other medication. The pad or disc 452 can be impregnated with medication and can be effective in either a moist or dry condition. The antibacterial medication can include, for example, liposomes and/or microspheres. The pad or disc 452 can be removably secured to the compress for single use or multiple uses. The pad can also be impregnated with materials to improve the aesthetics of the eye, like Vitamin E.

In example embodiments, the medication pad or disc 453 is moist-heat-transmissive, and application of moist-heat activates the release of the impregnated medication from the pad 452 onto the skin surface of the eyelid or other tissue in or around the user's eyes. In example forms, the pad or disc is constructed to prevent the impregnated medication from passing back into the compress during application. For example, a one-way sheet barrier material can be placed between the pad or disc and the compress to prevent any antibacterial medication from the disc from entering the compress.

In example embodiments, the medication pad or disc 452 can have a round or oval disc shape with appropriate size and shape to be placed over a single eyelid or attached to a single eye coverage portion 422. In use, two pads or discs can be used, one attached to each eye coverage portion 422. A plurality of discs can be stored within a container containing antibacterial medication fluid, so as to pre-moisten the discs during storage. In an exemplary manner of use, two discs are removed from the container and one is placed over each eye of a patient while the patient is lying down and the mask is placed over the discs so that the discs are held in between the eye and the eye coverage portion. Alternatively, the disc 452 may be attached to the detachable pod 450, such that when the eye mask or compress is worn, the disc rests in between the eyelid and the detachable pod. In other embodiments, the disc 452 is placed in the receiver 430 with the detachable pod 450.

In other example embodiments, the medicated disc is used as an eyelid cleaning or treatment wipe. The medicated disc is impregnated with a dry specialized formula that is activated by the heat and moisture from the mask. The medication assists in preparing debris in the eye for removal. The disc can then be removed from the mask and used to scrub or wipe the eye area, removing the debris. The disc can be formed of a scrim or non-woven material that accepts dry impregnation of specialized formulas or medication. Ideally, the medicated disc allows the passage of moisture and heat. The medicated disc can remove oil debris and pollen from the eyelids and enhance the moisture of the skin around the eye. The disc can also protect the mask itself from make-up or other contaminants.

Figure 19:
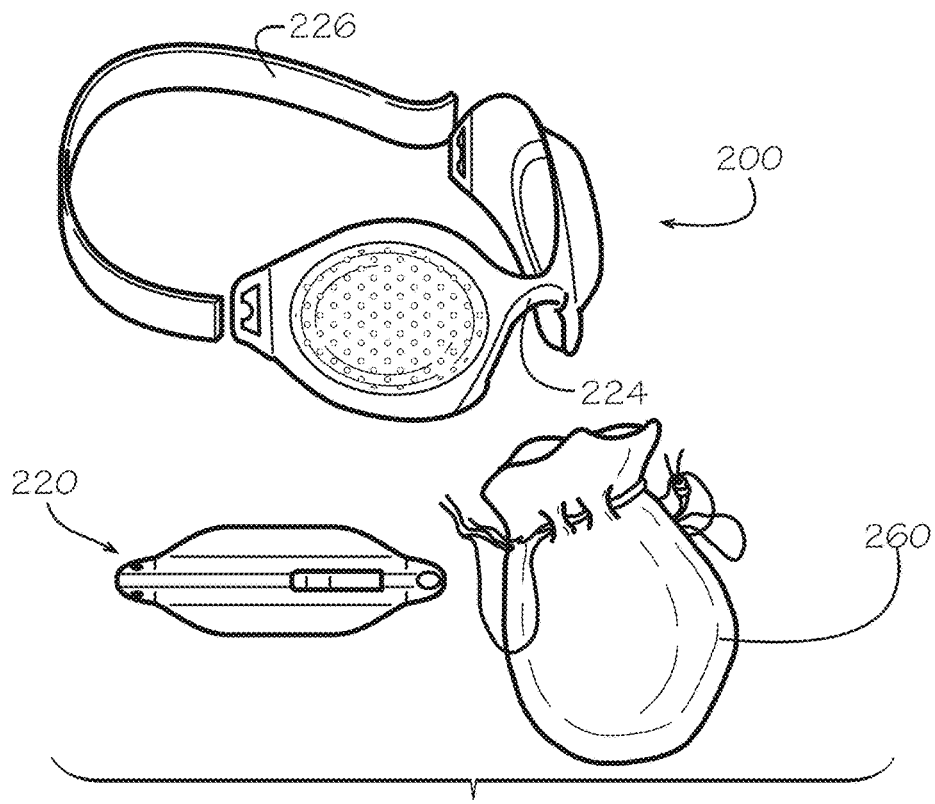
FIG. 19 shows a therapeutic eye mask system according to an example embodiment of the invention.
Figure 20:
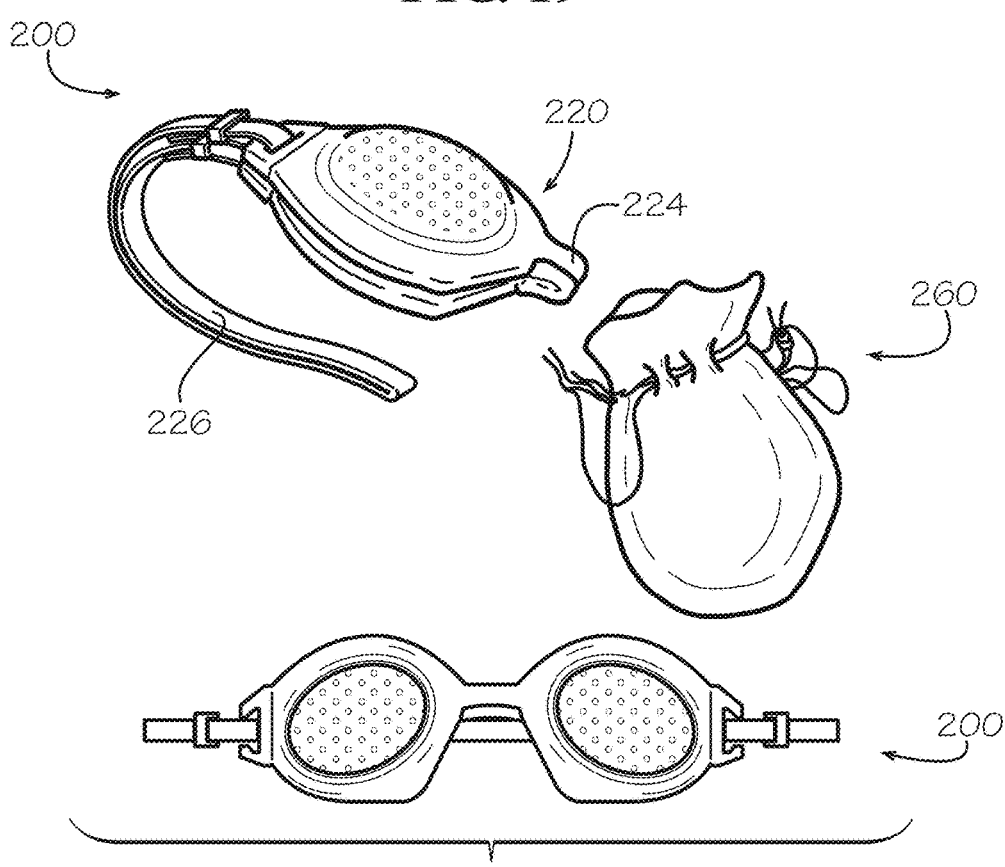
FIG. 20 shows a therapeutic eye mask system according to an example embodiment of the invention.
Figure 24:
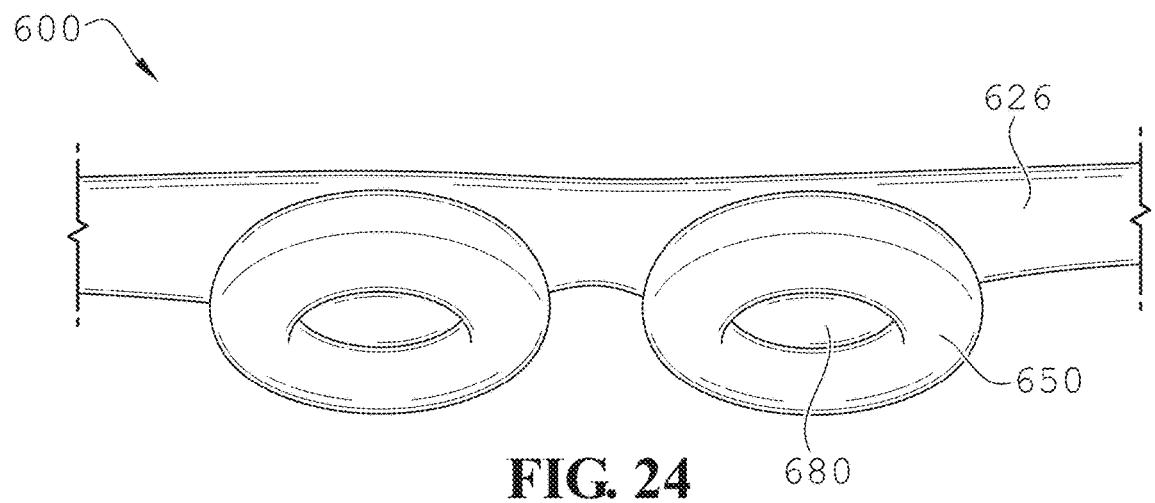
FIG. 24 is a perspective view of a therapeutic eye mask system according to another example embodiment of the invention.
Figure 25:
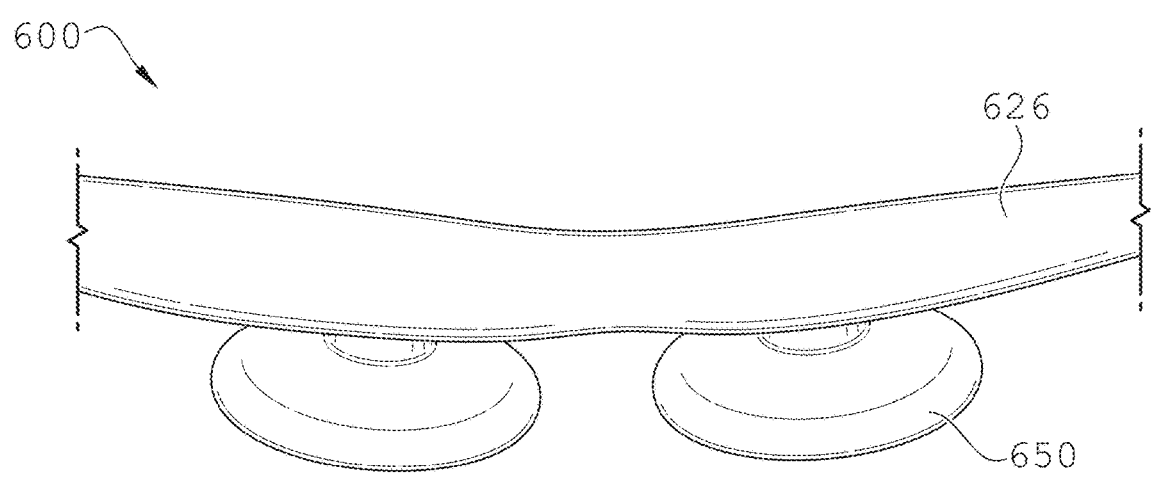
FIG. 25 shows a side view of the therapeutic eye mask system of FIG. 24.

The therapeutic eye mask system 200 can also include a storage bag 260, as shown in FIGS. 19 and 20. In the depicted embodiment the mask portion 220 is configured to fold at the flexible nose bridge 224 to fit within the storage bag 260. The securing strap 226 can be detached from the mask 220 for storage, as shown in FIG. 19, or the mask 220 can be stored with the securing strap 226 attached, as shown in FIG. 20.

FIGS. 21-23 show a mask 500 according to another example embodiment of the present invention. In the depicted embodiment, each eye coverage portion 522 includes an opening, recess, depression, slit or another void 580 configured to be positioned over the wearer's corneas when the mask is worn. Temperatures over 39.5° Celsius may be unsafe for the cornea. The openings or voids 580 positioned over and around the cornea can help prevent the application of excess heat on and around the cornea, preventing conditions such as corneal warping, while allowing moist heat therapy to reach the eyelid and surrounding eye area. In example embodiments, the cornea voids 580 are around 15 mm wide. In example embodiments, the voids 580 can be recessed in the eye coverage portion 522 or detachable pods or alternatively can be slits or openings extending through the entire thickness of the eye coverage portion and detachable pods whereby the user can see through the openings when worn. In alternate embodiments, the eye coverage portions or detachable pods can include a heat insulating material applied over one or more portions of the eye covers configured to be positioned over the corneas when in use. For example, an insulating shield can be attached to the central regions of each eye cover 522 or detachable pod. The insulating shield is configured to vault the cornea and prevent the application of excess heat on or around the corneas. This embodiment can further include an adjustable, flexible nose bridge 524. The adjustable nose bridge 524 allows the user to adjust the spacing distance between eye coverage portions 522 and/or between the voids in each eye cover to accommodate varying distances between human eyes from one individual to the next. The average pupillary distance for a human is around 57 mm to 65 mm. In example embodiments, the adjustable nose bridge 524 can be changed to accommodate a distance between cornea areas ranging from about 45 millimeters to about 74 millimeters. This range is sufficient to accommodate the eye placement of the majority of adult and/or child male and female humans. In example embodiments, one or more adjustable or expandable straps or bands are provided between the eye covers to allow adjustment of the relative positions or spacing of the eye covers. Alternatively, the eye covers can be detachably mounted to the retention strap, for example with hook-and-loop fastener material, to allow for repositioning of the eye covers on the strap to vary the spacing and position of the eye covers.

Figure 26:
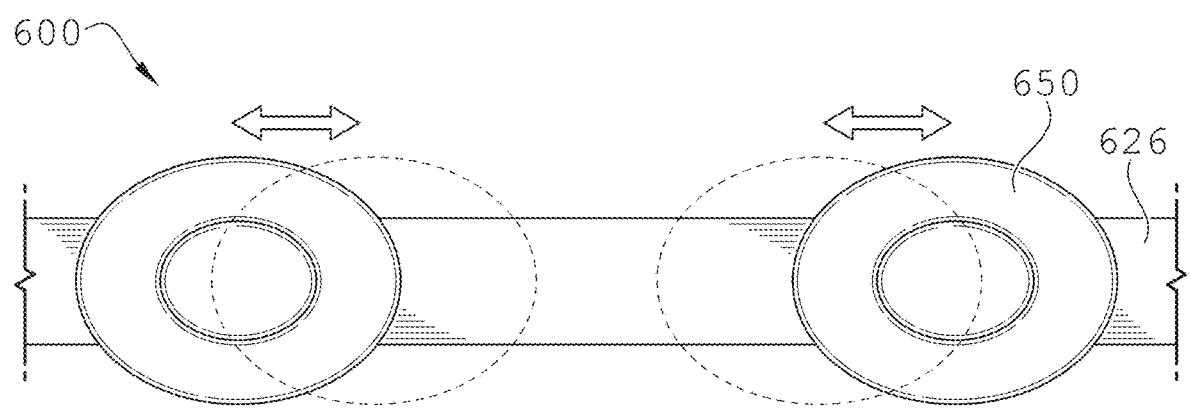
FIG. 26 shows a back view of the therapeutic eye mask system of FIG. 24.
Figure 27:
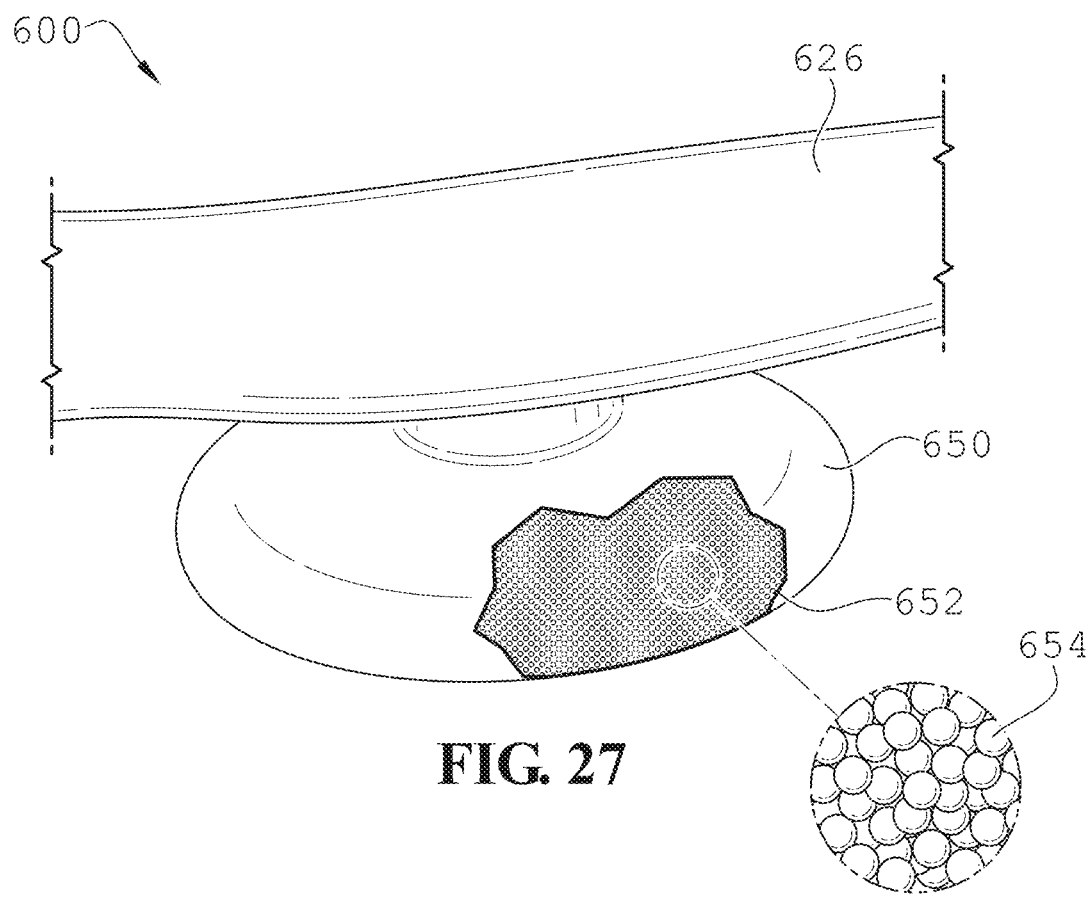
FIG. 27 is a cut-away view of a pod of the therapeutic eye mask system of FIG. 24.

FIGS. 24-27 show a therapeutic eye mask system 600 according to another example embodiment of the invention. The eye mask system 600 generally includes a mask portion or strap 626 and one or more pods 650 that are detachably secured to the strap. In this embodiment, the pods 650 are attached directly to the strap 626 without the need for a receiver as in previous embodiments. The strap 626 is positioned around the user's head to hold the pods 650 in contact with the eye area of the user. The pods 650 are releasably attached to the strap 626 using an attachment mechanism such as snaps, ties, hook-and-loop fasteners or other releasable attachment mechanisms. The pods 650 are attached directly to the strap 626 such that the back side of each pod directly contacts the front of the strap. The front of each pod 650 faces away from the strap 626 and is configured for contact with the eye area of the patient. In example embodiments, the pods 650 can be attached at a plurality of points along the strap 626, as shown in FIG. 26, such that the user can adjust the pods to fit their unique face shape. The pods 650 can also be used independently of the strap 626.

The pods 650 can also include a divot, recess, depression, or other void 680 configured to be positioned over the wearer's corneas when the mask is worn. As explained above, high temperatures may be unsafe for the cornea and the divot or recess 580 positioned over and around the cornea can help prevent the application of excess heat on and around the cornea, preventing conditions such as corneal warping, while allowing heat therapy to reach the eyelid and surrounding eye area.

As in previous embodiments, the pods 650 comprise an outer shell 652 that surrounds and contains a fill material 654. The pod shell 652 is formed from a flexible material such as a fabric. In example embodiments, the pod shell 652 is formed, in whole or in part, from a material with antimicrobial properties. The pod shell 652 material can incorporate an antimicrobial substance, such as silver or other antimicrobial metals. In example embodiments, silver salts or particles are attached to the pod shell fabric. In other embodiments, silver salts or particles are incorporated into fabric fibers such as polyester fibers. The silver particles are encapsulated by the plastic which protects them during manufacturing and use of the mask. The silver impregnated yarn is woven into the fabric of the pod shell 652. The silver impregnated yarn helps ensure that the antimicrobial silver particles are distributed throughout the pod shell 652. The mask can maintain its antimicrobial properties through repeated uses and launderings. The antimicrobial material is configured to kill bacteria in and around the user's eye by contact. In example embodiments, the antimicrobial material will kill 99% of bacteria after 4 hours of contact. In example embodiments, the section of the pod shell 652 that contacts the user's face includes the antimicrobial fibers. In other embodiments, the entire pod shell 652 is formed from a material incorporating antimicrobial fibers. In example embodiments, other components of the mask, such as the strap, are also formed from an antimicrobial material as described above.

The fill material 654 generally comprises a plurality of fill beads or granules. The fill material 654 is contained by the pod shell 652 such that it remains within the shell and does not fall out. The fill material 654 is generally able to move within the pod shell 652 such that the shape of the pod 650 will conform to the face of the user. In example embodiments, the fill beads or granules 654 can be formed from a resilient, deformable material, such as silicon. The resilient, deformable fill beads contribute to the comfort of the user.

Figure 28:
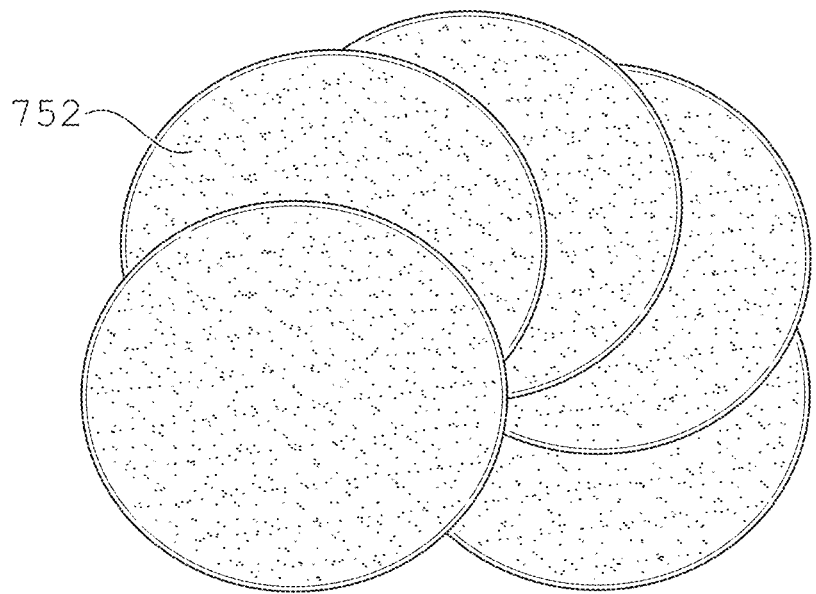
FIG. 28 shows heat-transmissive pads for use with a therapeutic eye mask.
Figure 29:
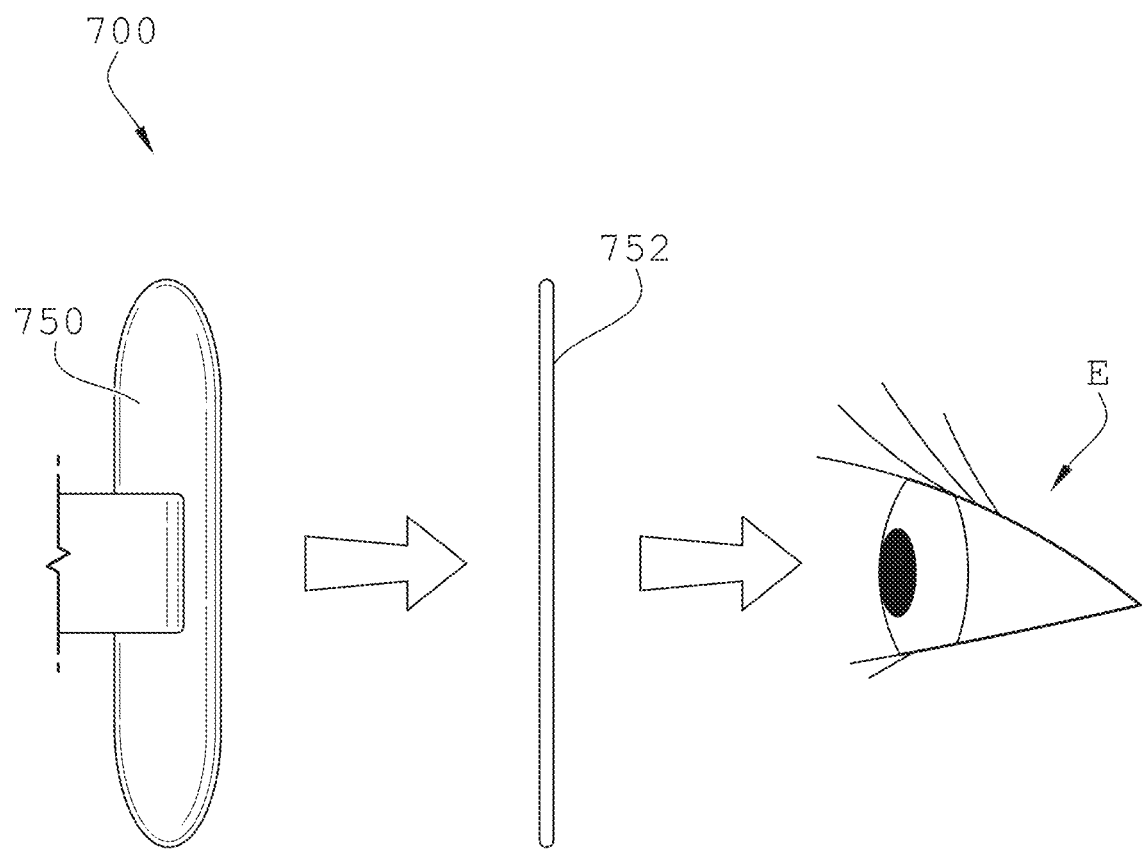
FIG. 29 shows a side exploded view of a therapeutic eye mask system with heat-transmissive pads.

FIGS. 28-29 show a therapeutic eye mask system 700 according to another example embodiment of the invention. The mask system 700 includes a therapeutic mask similar to those described above. The mask system 700 also includes a treatment sheet 752 that can be placed between the eye E of the user and the pod 750 or eye coverage portion. The treatment sheet 752 is generally impregnated with a unique therapeutic formula designed for a specific treatment of the eye area E of a patient. In example embodiments, the treatment sheet 752 is heat-transmissive, such that when the treatment sheet is heated or exposed to a heat source, the impregnated medication is released from the sheet and is able to travel to the eye area of the patient. The treatment sheets can be dry when impregnated with medication. These treatment sheets or pads can be used with a dry heat source. These treatment sheets 752 do not have to be stored in an air-tight container to prevent drying out. These treatment sheets also can be used without having to wet the sheet prior to use.

In example embodiments, the treatment sheets 752 can be a heat-transmissive pad or lid scrub or disc that is applied to the skin surface on the eyelid and around the eye E. The pad or disc 752 can be constructed of non-woven material and optionally a material that can be RF or thermally sealed to hold an antibacterial or other medication. The pads or sheets 752 can be formed from any material that accepts treatment materials and holds them in a dry state until activated by moisture and/or heat. The pad or disc can be impregnated with medication and can be effective in either a moist or dry condition.

In example embodiments, the medication pad or disc is moist-heat-transmissive, and application of moist-heat source activates the release of the impregnated medication onto the skin surface of the eyelid or other tissue in or around the user's eyes. In example forms, the pad or disc is constructed to prevent the impregnated medication from passing through the back of the disc away from the treatment area. For example, a one-way sheet barrier material can be placed between the pad or disk and the compress to prevent any antibacterial medication from the disk from entering the compress.

In example embodiments, the treatment pad or disk 752 can have a round or oval shape, as shown in FIG. 28. The treatment disk 752 is generally a size and shape to be placed on over a single eyelid. In use, two pads or disks can be used, one treats each eye. In alternate embodiments, the sheets can be shaped to cover the entire eye treatment area. A plurality of disks can be stored within a container containing antibacterial medication fluid, so as to pre-moisten the disks during storage. In other embodiments, a medication can be sprayed on the treatment pads prior to use.

In an exemplary manner of use, two disks are removed from the container and one is placed over each eye of a patient while the patient is lying down. The disk or sheet is exposed to a heat source, causing the impregnated medication to be released towards the eye. Alternatively, the disk may be detachably or permanently attached to a reusable or disposable compress delivering dry or moist heat, such that when the eye mask or compress is worn, the disk rests in between the eyelid and the detachable pod. The pad or sheet can include a means for attaching the pad to a compress. Attachment means can include an adhesive material or a fastening device such as a hook and loop fastener. In alternate embodiments, the pad or sheet can be activated by another device producing dry or moist heat, such as a humidifier, a steam or water vapor generator, a heating pad, etc.

Examples of medicants or therapeutic materials capable of delivery using the therapeutic device according to example forms of the invention include a jojoba formulation for treatment of the symptoms of dry eye, steroids such as clobetasol propionate, betamethasone dipropionate, amcinonide or loteprednol etabonate for treatments of diseases of the eyelid, such as chatazion, blepharitis or meibomian gland dysfunction. The medicant can include honey, for example, manuka honey. The medicant or medication can include natural oils including coconut or tea tree oils for the treatment of conditions including Blepharitis. The medicant can be an antibacterial medication including, for example, liposomes and/or microspheres. Medicants may also comprise a dietary or nutritional supplement composition comprising an effective amount of omega-3 fatty acids for treatment of dry eye or meibomianitis. Medicants may also comprise tetracycline, corticosteroids, androgens or androgen analogues. The medicant may also comprise a topical treatment to elevate the side effects of chemotherapy, including eyelash loss. The medicant can include menthol configured to stimulate lacrimoation via activation of cold-sensitive primary afferent neurons in the cornea. Repeated use of menthol can induce persistent increases in tear fluid volume and tear film stability in dry eye patients.

In further embodiments, the therapeutic device takes the form of a hygienic cleaning sheet or pad, including a heat-transmissive substrate configured for cleaning away makeup, debris, oils, contaminants or other materials from a user's eyelids, eyelashes, and surrounding tissue. The sheet or pad may be utilized for hygienic cleansing before, during and/or after application of heat. The substrate is optionally dry coated with one or more natural oils or other hygienic cleansing materials such as for example coconut or tea tree oils, manuka or other honey, menthol, and/or vitamin E. The natural oils or other hygienic cleansing materials optionally provide antibacterial or antimicrobial treatment. In example embodiments, the natural oils or other hygienic cleansing materials are dry coated onto/into the substrate, and configured for release from the substrate toward and onto the eyelids and surrounding tissue or other body parts of a human or animal user, upon application of heat (including moist heat) to the therapeutic device and/or the targeted tissue or body part(s). The natural oils or other hygienic cleansing materials are preferably activated to therapeutically effective levels by application of heat (including moist heat) at safe and comfortable temperatures and moisture levels.

While the invention has been described with reference to preferred and example embodiments, it will be understood by those skilled in the art that a variety of modifications, additions and deletions are within the scope of the invention, as defined by the following claims.

What is claimed is:

1. A therapeutic mask system for treatment of an eye region of a human or animal subject's head, the system comprising:
   a strap configured for positioning the strap around the subject's head, the strap comprising a first side a second side opposite the first side, a first end, a second end, and a center portion between the first end and the second end; and
   at least one treatment pod containing a loose, granular fill material within an outer shell, the at least one treatment pod comprising a first side and a second side opposite the first side;
   wherein the center portion of the strap spans at least across the at least one treatment pod,
   wherein only the second side of the at least one treatment pod is releasably coupled to the center portion of the strap on the first side of the strap,
   wherein the at least one treatment pod comprises a recessed area formed on the first side of the at least one treatment pod, and
   wherein the first side of the at least one treatment pod is configured for contact with the eye region of the subject's head.

2. The therapeutic mask system of claim 1, wherein the outer shell of the at least one treatment pod is formed from a fabric material.

3. The therapeutic mask system of claim 2, wherein at least a portion of the fabric material of the at least one treatment pod comprises an antimicrobial material embedded in the fabric material.

4. The therapeutic mask system of claim 3, wherein the antimicrobial material comprises yarn comprising silver particles and wherein the silver yarn is woven into at least a portion of the fabric material of the outer shell.

5. The therapeutic mask system of claim 1, wherein the at least one treatment pod is configured to be releasably coupled to the strap at a plurality of points along the strap.

6. The therapeutic mask of claim 1, wherein the at least one treatment pod is configured to deliver heat to the eye region of the subject.

7. The therapeutic mask system of claim 1, wherein the at least one treatment pod is configured to deliver cold therapy to the eye region of the subject.

8. The therapeutic mask system of claim 1, wherein the at least one treatment pod is configured to deliver moist heat to the eye region of the subject's head.

9. The therapeutic mask system of claim 1, wherein the loose, granular fill material comprises a hydrophilic zeolite.

10. The therapeutic mask system of claim 1, wherein the recessed area is an indentation on the first side of the at least one treatment pod.

11. The therapeutic mask system of claim 1, wherein the recessed area is an opening.

12. The therapeutic mask system of claim 1, wherein the therapeutic mask system further comprises an insulating shield and wherein the insulating shield is configured to be positioned between the at least one treatment pod and the cornea of the at least one eye of the subject.

13. The therapeutic mask system of claim 1, wherein the at least one treatment pod is releasably coupled to the strap by snap fasteners or hook-and-loop fasteners.

14. The therapeutic mask system of claim 1, wherein the strap is receiver-less and the at least one treatment pod is detachably secured directly to the strap.

* * * * *